US011820729B2

(12) United States Patent
Gambogi et al.

(10) Patent No.: US 11,820,729 B2
(45) Date of Patent: *Nov. 21, 2023

(54) AMINO ACID DERIVATIVES AND THEIR USES

(71) Applicant: Johnson & Johnson Consumer Inc., Skillman, NJ (US)

(72) Inventors: Robert J. Gambogi, Hillsborough, NJ (US); Anthony R. Geonnotti, III, Princeton, NJ (US); Michael C. Giano, Southampton, NJ (US); Latrisha Petersen, Highland Park, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 12 days.

This patent is subject to a terminal disclaimer.

(21) Appl. No.: 17/337,649

(22) Filed: Jun. 3, 2021

(65) Prior Publication Data

US 2021/0284604 A1  Sep. 16, 2021

Related U.S. Application Data

(60) Continuation of application No. 16/691,330, filed on Nov. 21, 2019, now Pat. No. 11,046,643, which is a continuation of application No. 15/955,798, filed on Apr. 18, 2018, now abandoned, which is a division of application No. 14/938,334, filed on Nov. 11, 2015, now Pat. No. 9,975,847.

(60) Provisional application No. 62/078,187, filed on Nov. 11, 2014.

(51) Int. Cl.
*C07C 279/12* (2006.01)
*A61K 8/43* (2006.01)
*A61Q 11/00* (2006.01)
*C07C 237/22* (2006.01)
*A61K 8/44* (2006.01)

(52) U.S. Cl.
CPC ............ *C07C 279/12* (2013.01); *A61K 8/43* (2013.01); *A61K 8/44* (2013.01); *A61Q 11/00* (2013.01); *C07C 237/22* (2013.01)

(58) Field of Classification Search
CPC ......... A61K 8/44; A61Q 11/00; C07C 237/22
See application file for complete search history.

(56) References Cited

U.S. PATENT DOCUMENTS

| | | |
|---|---|---|
| 4,051,234 A | 9/1977 | Gieske et al. |
| 4,994,262 A | 2/1991 | Charbonneau et al. |
| 5,190,747 A | 3/1993 | Sekiguchi et al. |
| 5,328,682 A | 7/1994 | Pullen et al. |
| 5,874,068 A | 2/1999 | Engleman et al. |
| 6,121,315 A | 9/2000 | Nair et al. |
| 6,416,745 B1 | 7/2002 | Markowitz et al. |
| 6,682,722 B2 | 1/2004 | Majeti et al. |
| 7,084,104 B2 | 8/2006 | Martin et al. |
| 7,087,650 B2 | 8/2006 | Lennon |
| 7,417,020 B2 | 8/2008 | Fevola et al. |
| 8,084,449 B2 | 12/2011 | Callahan et al. |
| 8,518,994 B2 | 8/2013 | Wakita et al. |
| 9,975,847 B2 * | 5/2018 | Gambogi ............... A61Q 11/00 |
| 2003/0050247 A1 * | 3/2003 | Kuhner ................... A61P 31/06 |
| | | 530/331 |
| 2003/0194445 A1 | 10/2003 | Kuhner et al. |
| 2004/0258630 A1 | 12/2004 | Boyd et al. |
| 2004/0258632 A1 | 12/2004 | Boyd et al. |

(Continued)

FOREIGN PATENT DOCUMENTS

| | | |
|---|---|---|
| JP | 5982310 | 5/1984 |
| WO | WO2000/011022 | 2/2000 |
| WO | WO 2001/098362 | 12/2001 |
| WO | WO2003/013454 | 2/2003 |
| WO | WO 2005/000261 A1 | 1/2005 |

(Continued)

OTHER PUBLICATIONS

Pinazo, A.; New cationic vesicles prepared with double chain surfactants fromarginine: Role of the hydrophobic group on the antimicrobial activityand cytotoxicity; Colloids and Surfaces B: Biointerfaces 141 (2016) 19-27.

(Continued)

*Primary Examiner* — Mark V Stevens
(74) *Attorney, Agent, or Firm* — Darryl C. Little

(57) ABSTRACT

Provided are compounds described by the Formula I:

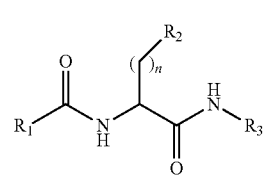

(I)

wherein: $R_1$ is a linear or branched, saturated or unsaturated aliphatic group having from 5 to 22 carbon atoms; $R_2$ is selected from the group consisting of the functional groups:
—$NH_2$;

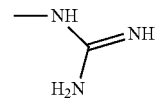

and salts thereof; n is from 0 to 4; and $R_3$ is a linear or branched, saturated or unsaturated aliphatic group having from 1 to 6 carbon atoms. Also provided are compositions comprising, and methods of use of, the compounds of the present invention.

4 Claims, 3 Drawing Sheets

(56) References Cited

U.S. PATENT DOCUMENTS

| | | |
|---|---|---|
| 2005/0027001 A1 | 2/2005 | Boyd |
| 2006/0013778 A1 | 1/2006 | Hodosh |
| 2008/0317839 A1 | 12/2008 | Quay |
| 2010/0330136 A1 | 12/2010 | Rocabayera Bonvila |

FOREIGN PATENT DOCUMENTS

| | | |
|---|---|---|
| WO | WO2008/137758 A2 | 11/2008 |

OTHER PUBLICATIONS

International Search Report dated Jan. 21, 2016;—Int'l. Appln. No. PCT/US2015/060166 filed Nov. 11, 2015.
Morrison and Boyd, Organic Chemistry Fourth Edition, section 20.3, p. 814.
Yang Xu and R. F. Pratt, "β—Lactam-Recognizing Enzymes Exhibit Different Structural Specificity in Acyclic Amide and Ester Substrates: A Starting Point in B-Lactamase Evolution?" Bioorganic & Medicinal Chemistry Letters, vol. 4. No. 19. pp. 2291-2296 (1994).
Zhaozhao Li, et al. "Peptide a-Keto Ester, a-Keto Amide, and a-Keto Acid Inhibitors of Calpains and Other Cysteine Proteases" J. Med. Chem. 1993,36, 3472-3480.
Kazuhiko, et al. JPS 5982310 (A)(1984) English Abstracts.
Ammann (AAPS PharmSciTech, 2011, vol. 12, pp. 1264-1275) (Year: 2011).
Engeloch et al. (Journal of Biological Screening, 2008, vol. 13, pp. 999-1006) (Year: 2008).

* cited by examiner

AMINO ACID DERIVATIVES AND THEIR USES

CROSS REFERENCE TO RELATED APPLICATION

The present application is continuation of U.S. patent application Ser. No. 16/691,330, filed Nov. 21, 2019, which is a continuation of U.S. patent application Ser. No. 15/955,798, filed Apr. 18, 2018, which is a divisional of U.S. patent application Ser. No. 14/938,334 filed Nov. 11, 2015, which claims the benefit of U.S. Provisional Application No. 62/078,187, filed Nov. 11, 2014.

BACKGROUND

A variety of amino acid derivatives are known in the art for a variety of uses. For example, U.S. Pat. No. 5,874,068, WO2003/013454, and US2010/0330136 disclose the use of Lauryl arginine ethyl ester ("LAE"), and certain related compounds, for use in oral compositions. In addition, LAE is currently used in hydroalcoholic mouth rinses to prevent bacterial attachment. However, applicants have recognized that LAE tends to lack sufficient stability to be useful in low-alcohol or alcohol-free mouth rinses.

In addition, other documents such as WO2008/137758A2 and WO2000/011022 disclose broad classes of compounds, which may include certain amino acid derivatives, for uses such as for drug delivery or anti-tumor end benefits, respectively.

DESCRIPTION OF THE INVENTION

Figure 1:
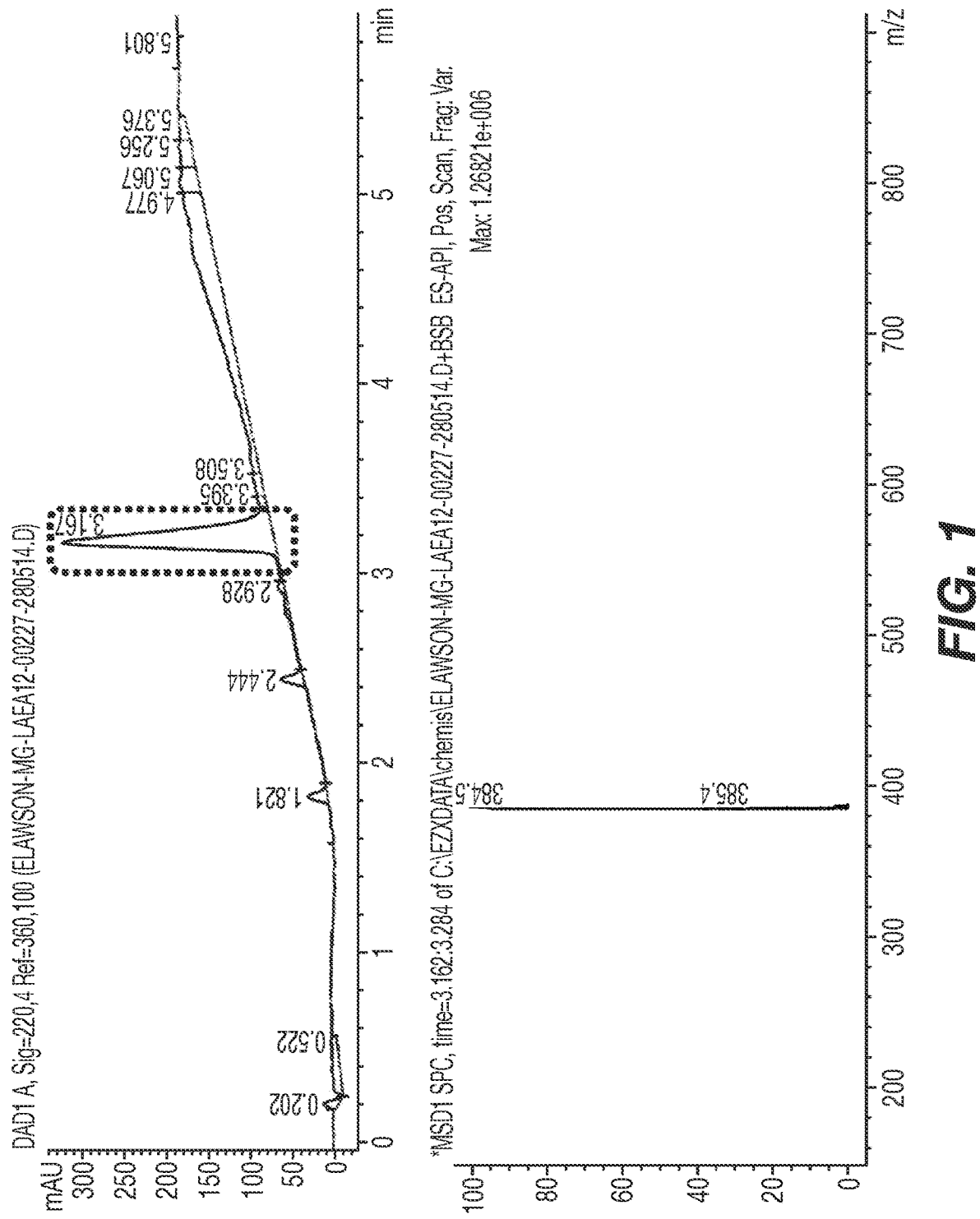
FIG. 1 is an HPLC chromatograph and a mass spectrometry graph of [amino({[4-dodecanamido-4-(ethylcarbamoyl)butyl]amino})methylidene]azanium.

The present invention relates to new amino acid derivatives developed by applicants that are described by the Formula I:

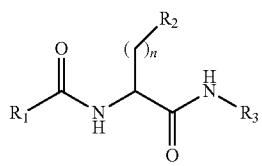

(I)

wherein:

$R_1$ is a linear or branched, saturated or unsaturated aliphatic group having from 5 to 22 carbon atoms;

$R_2$ is selected from the group consisting of the free base and corresponding salt forms of the functional groups: $-NH_2$;

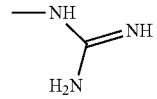

said salt versions having an anion $X^-$ preferably selected from the group consisting of acetate, benzoate, besylate, bromide, chloride, chlortheophyllinate, citrate, ethandisulfonate, fumarate, gluconate, hippurate, iodide, fluoride, lactate, laurylsulfate, malate, laeate, mesylate, methysulfate, napsylate, nitrate, octadecanoate, oxalate, pamoate, phosphate, polygalacturonate, succinate, sulfate, tartrate, and tosylate;

n is from 0 to 4; and $R_3$ is a linear or branched, saturated or unsaturated aliphatic group having from 1 to 6 carbon atoms.

The compositions of Formula I may have any suitable linear or branched, saturated or unsaturated aliphatic group having from 5 to 22 carbons for $R_1$. Examples of suitable linear or branched, saturated or unsaturated aliphatic groups having from 5 to 22 carbons include, $C_5$ to $C_{22}$ linear or branched alkyl groups, such as, pentyl, hexyl, heptyl, octyl, nonyl, decyl, undecyl, dodecyl, up to docosanyl, and the like; as well as, $C_5$ to $C_{22}$ linear or branched alkylene groups such as myristolyl up to docasanhexayl, and the like.

In certain embodiments, $R_1$ is linear or branched alkyl group having a carbon chain of from 5 to 22 carbons atoms, including for example, pentyl, hexyl, heptyl, octyl, nonyl, decyl, undecyl, dodecyl up to docasonyl. In certain other embodiments, $R_1$ is linear or branched alkyl group having a carbon chain of from 7 to 18 carbons atoms, including for example, heptyl, octyl, nonyl, decyl, undecyl, dodecyl, tridecyl, tetradecyl, pentadecyl, hexadecyl, heptadecyl and octadecyl. In still other embodiments, $R_1$ is linear or branched alkyl group having a carbon chain of from 9 to 14 carbons atoms, including for example, decyl, undecyl, dodecyl up to tetradecyl. In certain embodiments, $R_1$ is an undecyl group. In certain embodiments, $R_1$ is a heptyl group. In certain embodiments, $R_1$ is a heptadecyl group.

In certain embodiments, $R_1$ is linear or branched alkenyl group having a carbon chain of from 5 to 22 carbons atoms, including for example, 9-hexadecenyl, 9-octadecenyl, 11-decenyl, 9,12-octadecandienyl, 9,12,15-octadecatrienyl, 6,9,12-octadecatrienyl, 9-eicosenyl, 5,8,11,14-eicosatetraenyl, 13-docosenyl and 4,7,10,13,16,19-docosaheaenyl. In certain other embodiments, $R_1$ is linear or branched alkenyl group having a carbon chain of from 16 to 20 carbons atoms, including for example, 9-hexadecenyl, 9-octadecenyl, 11-decenyl, 9,12-octadecandienyl, 9,12,15-octadecatrienyl, and 6,9,12-octadecatrienyl.

In certain embodiments, $R_1$ is a branched alkyl group having a carbon chain of from 5 to 22 carbons atoms, including for example, 2-decyldodecanyl, 2-nonyltridecanyl, 2-octyltetradecanyl, 2-heptylpentadecanyl, 2-hexylhexadecanyl, 2-pentylheptadecanyl, 21-methylicosanyl, 18-ethylicosanyl, 16-propylnonadecyl, and 14-butyloctadecyl.

The compositions of Formula I may comprise an $R_2$ group that is an amine group in its free base form ($-NH_2$) or a salt thereof, or a guanidinyl functional group in its free base form ($-NH(CNH)NH_2$) or a salt thereof. Examples of suitable amine salts and guanidinyl salts include salts of such groups having an anion (X−) selected from the group consisting of acetate, benzoate, besylate, bromide, chloride, chlortheophyllinate, citrate, ethandisulfonate, fumarate, gluconate, hippurate, iodide, fluoride, lactate, laurylsulfate, malate, laeate, mesylate, methysulfate, napsylate, nitrate, octadecanoate, oxalate, pamoate, phosphate, polygalacturonate, succinate, sulfate, tartrate, and tosylate. In certain embodiments, the composition of the present invention has an $R_2$ group that is an amine group in its free base form (—$NH_2$). In certain other embodiments, the composition of the present invention has an $R_2$ group that is an a guanidinyl group in its free base form (—$NH(CNH)NH_2$). In certain embodiments, the composition of the present invention has an $R_2$ group that is an amine salt having an anion selected from the group consisting of acetate, benzoate, besylate, bromide, chloride, chlortheophyllinate, citrate, ethandisulfonate, fumarate, gluconate, hippurate, iodide, fluoride, lactate, laurylsulfate, malate, laeate, mesylate, methysulfate, napsylate, nitrate, octadecanoate, oxalate, pamoate, phosphate, polygalacturonate, succinate, sulfate, tartrate, and tosylate. In certain other embodiments, the $R_2$ amine salt has an anion selected from the group consisting of acetate, benzoate, bromide, chloride, citrate, fumarate, gluconate, iodide, fluoride, lactate, malate, nitrate, oxalate, phosphate, sulfate, and in certain other embodiments an anion selected from the group consisting of bromide, chloride, iodide, fluoride, oxalate, and phosphate. In addition, in certain embodiments, the composition of the present invention has an $R_2$ group that is a guanidinyl salt having an anion selected from the group consisting of acetate, benzoate, besylate, bromide, chloride, chlortheophyllinate, citrate, ethandisulfonate, fumarate, gluconate, hippurate, iodide, fluoride, lactate, laurylsulfate, malate, laeate, mesylate, methysulfate, napsylate, nitrate, octadecanoate, oxalate, pamoate, phosphate, polygalacturonate, succinate, sulfate, tartrate, and tosylate. In certain other embodiments, the $R_2$ guanidinyl salt has an anion selected from the group consisting of acetate, benzoate, bromide, chloride, citrate, fumarate, gluconate, iodide, fluoride, lactate, malate, nitrate, oxalate, phosphate, sulfate, and in certain other embodiments an anion selected from the group consisting of bromide, chloride, iodide, fluoride, oxalate, and phosphate.

The compositions of Formula I may have any suitable linear or branched, saturated or unsaturated aliphatic group having from 1 to 6 carbons for $R_3$. Examples of suitable linear or branched, saturated or unsaturated aliphatic groups having from 1 to 6 carbons include, $C_1$ to $C_6$ linear or branched alkyl groups, such as, methyl, ethyl, propyl, isopropyl, butyl, isobutyl, sec-butyl, tert-butyl, pentyl, tert-pentyl, neopentyl, isopentyl, hexyl, isohexyl, neohexyl; as well as $C_2$ to $C_6$ linear or branched alkenyl groups such as vinyl, allyl, propenyl, butenyl, pentenyl, hexenyl, and the like. In certain embodiments, $R_3$ is linear or branched alkyl group having a carbon chain of from 1 to 4 carbons atoms, including for example, methyl, ethyl, propyl, isopropyl, butyl, sec-butyl, isobutyl, and tert-butyl. In certain other embodiments, $R_3$ is linear or branched alkyl group having a carbon chain of from 1 to 3 carbons atoms, including for example, methyl, ethyl, propyl and isopropyl. In certain embodiments, $R_3$ is an ethyl group.

In certain embodiments, $R_3$ is linear or branched alkenyl group having a carbon chain of from 2 to 6 carbons atoms, including for example, vinyl, allyl, propenyl, butenyl, pentenyl, hexenyl, and the like as well as mixture thereof. In certain other embodiments, $R_3$ is linear or branched alkylene group having a carbon chain of from 2 to 4 carbons atoms, including for example, vinyl, allyl, propenyl, and butenyl.

In the compounds of Formula I, n can be from zero to four. In certain embodiments, n is from 1 to 4, in certain embodiments from 2 to 4, in certain embodiments 3 to 4. In certain particular embodiments, n is 0. In certain other embodiments n is 1, in other embodiments n is 2 in other embodiments n is 3 and in other embodiments n is 4.

According to certain embodiments of the invention, the compounds of Formula I are compounds wherein $R_2$ is a guanidinyl functional group in its free base form (—$NH(CNH)NH_2$) or a salt thereof; n is 3 or 4, preferably 3; $R_3$ is an aliphatic group having a carbon chain of about 2 carbons atoms, for example an ethyl group; and $R_1$ is a linear or branched, saturated or unsaturated aliphatic group, including for example an alkyl group, having from 9 to 16 carbon atoms, including from about 10 to about 16 carbon atoms, about 10 to about 15 carbon atoms, about 10 to about 14 carbon atoms, about 10 to about 13 carbon atoms, about 11 to about 14 carbon atoms, about 11 to about 15 carbon atoms, about 11 to about 16 carbon atoms, and about 11, and/or about 13 carbon atoms.

In certain other embodiments, the compounds of Formula I are compounds wherein $R_2$ is a guanidinyl functional group in its free base form (—$NH(CNH)NH_2$) or a salt thereof; n is 3; $R_1$ is a linear or branched, saturated or unsaturated aliphatic group, including for example an alkyl group, having about 11 carbon atoms; and $R_3$ is a linear or branched, saturated or unsaturated aliphatic group, including for example an alkyl group, having a carbon chain length of about 1 to 11 carbons atoms, including from about 2 to about 10 carbon atoms, about 2 to about 9 carbon atoms, about 2 to about 8 carbon atoms, about 3 to about 11 carbon atoms, about 3 to about 10 carbon atoms, about 3 to about 9 carbon atoms, about 3 to about 8 carbon atoms, and about 2, about 6, and/or about 8 carbon atoms.

In certain other embodiments, the compounds of Formula I are compounds wherein $R_2$ is a guanidinyl functional group in its free base form (—$NH(CNH)NH_2$) or a salt thereof; n is 3; $R_1$ is a linear or branched, saturated or unsaturated aliphatic group, including for example an alkyl group, having about 7 carbon atoms; and $R_3$ is a linear or branched, saturated or unsaturated aliphatic group, including for example an alkyl group, having a carbon chain length of about 7 to 16 carbons atoms, including from about 7 to about 15 carbon atoms, about 7 to about 14 carbon atoms, about 7 to about 13 carbon atoms, about 7 to about 12 carbon atoms, about 7 to about 11 carbon atoms, and about 7, and/or about 11 carbon atoms.

In certain other embodiments, the compounds of Formula I are compounds wherein $R_2$ is an amine group in its free base form (—$NH_2$) or a salt thereof; and n is 1, 3, or 4. Examples of such compounds include those wherein n is 3; $R_1$ is a linear or branched, saturated or unsaturated aliphatic group, including for example an alkyl group, having about 7 carbon atoms; and $R_3$ is a linear or branched, saturated or unsaturated aliphatic group, including for example an alkyl group, having a carbon chain length of about 1 to 11 carbons atoms, including from about 2 to about 10 carbon atoms, about 2 to about 9 carbon atoms, about 2 to about 8 carbon atoms, about 3 to about 11 carbon atoms, about 3 to about 10 carbon atoms, about 3 to about 9 carbon atoms, about 3 to about 8 carbon atoms, and about 8, and/or about 11 carbon atoms. Other Examples include compounds wherein n is 3; $R_1$ is a linear or branched, saturated or unsaturated aliphatic group, including for example an alkyl group, having about 11 carbon atoms; and $R_3$ is a linear or branched, saturated or unsaturated aliphatic group, including for example an alkyl group, having a carbon chain length of about 1 to 11 carbons atoms, including from about 1 to about 10 carbon atoms, about 1 to about 9 carbon atoms, about 1 to about 8 carbon atoms, about 1 to about 7 carbon atoms, about 1 to about 6 carbon atoms, about 2 to about 11 carbon atoms, about 2 to about 10 carbon atoms, about 2 to about 9 carbon atoms, about 2 to about 8 carbon atoms, about 2 to about 7 carbon atoms, about 2 to about 6 carbon atoms, and about 2 and/or about 6 carbon atoms.

One example of a compound of Formula I of the present invention is [amino({[4-dodecanamido-4-(ethylcarbamoyl)butyl]amino})methylidene]azanium (compound 9) as shown below.

As shown in the formula above, compound 9 represents a compound of Formula I wherein $R_1$ is an undecyl group, $R_2$ is a guanidinyl group in its free base form, $R_3$ is an ethyl group, and n is 3.

Other examples of compounds of the present invention include, but are not limited to compounds described by the formulae:

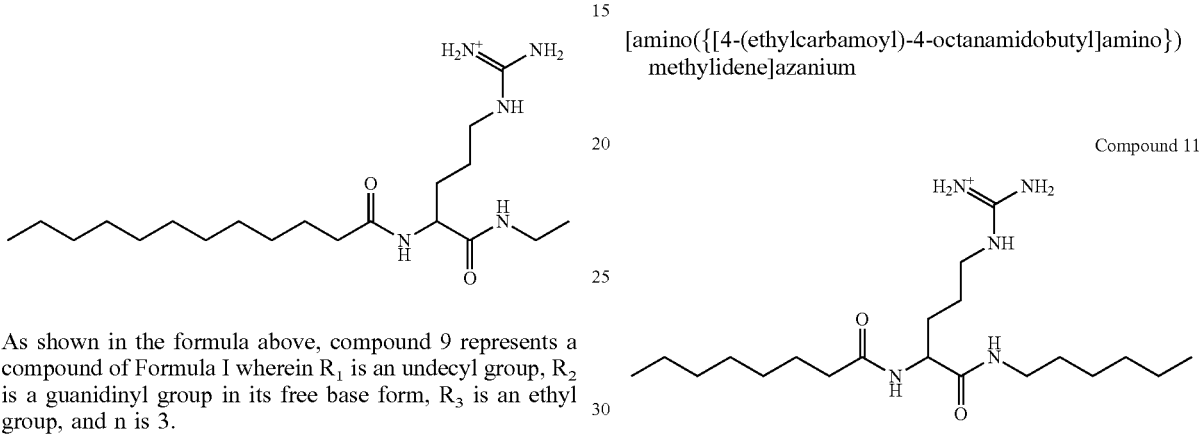

[amino({[4-(methylcarbamoyl)-4-octanamidobutyl]amino})methylidene]azanium

[amino({[4-(ethylcarbamoyl)-4-octanamidobutyl]amino})methylidene]azanium

[amino({[4-(hexylcarbamoyl)-4-octanamidobutyl]amino})methylidene]azanium

[amino({[4-dodecanamido-4-(methylcarbamoyl)butyl]amino})methylidene]azanium

[amino({[4-dodecanamido-4-(hexylcarbamoyl)butyl]
   amino})methylidene]azanium

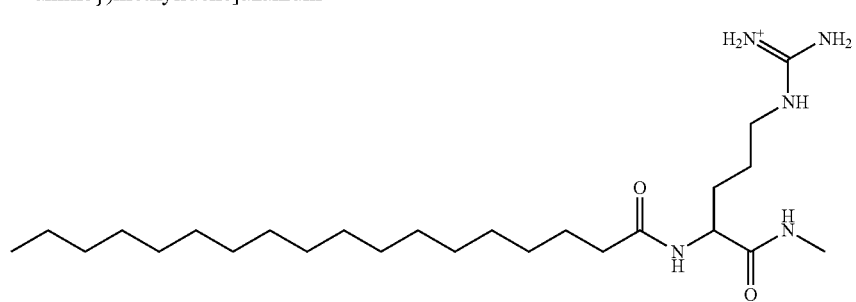
Compound 7

[amino({[4-(methylcarbamoyl)-4-octadecanamidobutyl]
   amino})methylidene]azanium

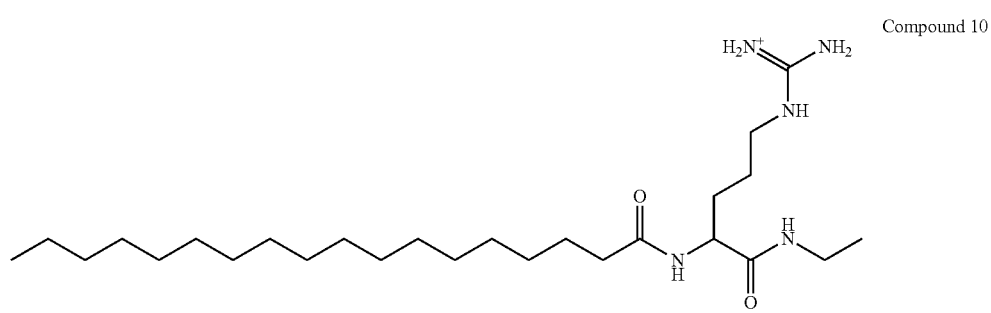 [SMILES: CCCCCCCCCCCCCCCCCC(=O)NC(CCCNC(N)=[NH2+])C(=O)NCC]
Compound 10

[amino({[4-(ethylcarbamoyl)-4-octadecanamidobutyl]
   amino})methylidene]azanium

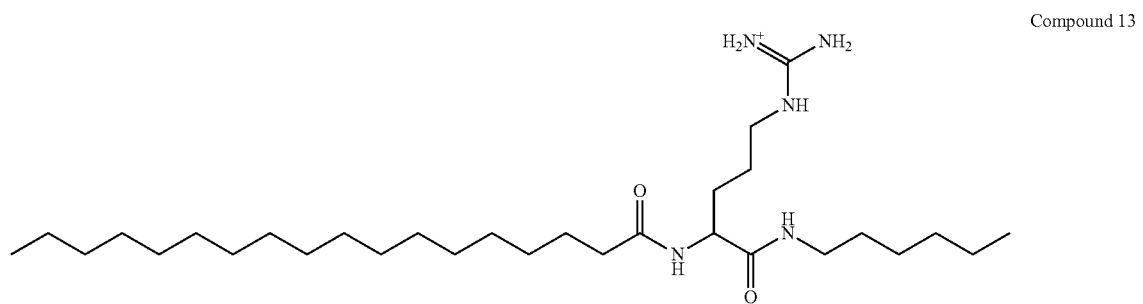 [SMILES: CCCCCCCCCCCCCCCCCC(=O)NC(CCCNC(N)=[NH2+])C(=O)NCCCCCC]
Compound 13

[amino({[4-(hexylcarbamoyl)-4-octadecanamidobutyl]
   amino})methylidene]azanium

[amino({[5-dodecanamido-5-(ethylcarbamoyl)pentyl]
   amino})methylidene]azanium

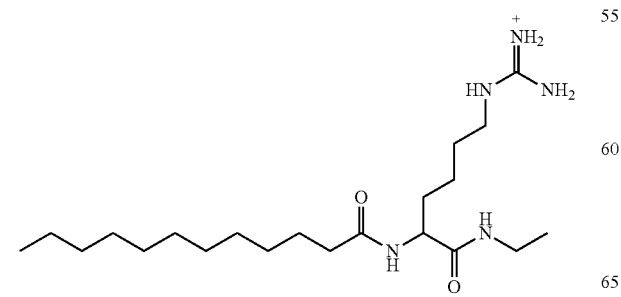
Compound 4

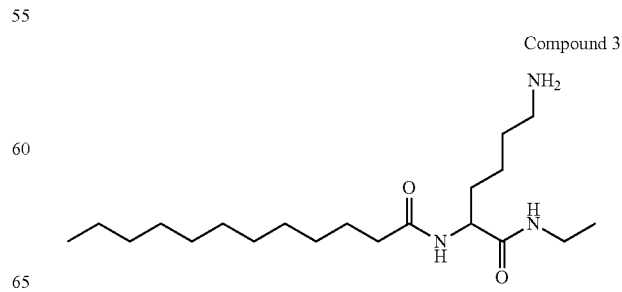
Compound 3

N-[5-amino-1-(ethylcarbamoyl)pentyl]dodecanamide 3-dodecanamido-4-(ethylamino)-4-oxobutanoic acid Compound 1

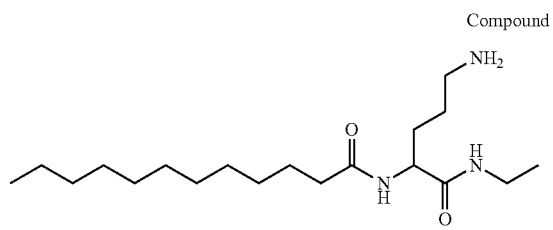

N-[4-amino-1-(ethylcarbamoyl)butyl]dodecanamide

Compound 15

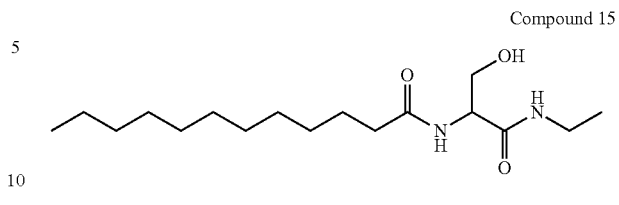

Compound 2

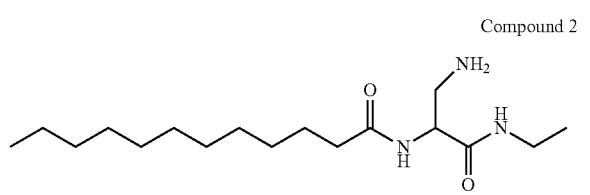 [SMILES: CCCCCCCCCCCC(=O)NC(CN)C(=O)NCC]

N-[2-amino-1-(ethylcarbamoyl)ethyl]dodecanamide

N-(1-(ethylamino)-3-hydroxy-1-oxopropan-2-yl)dodecanamide

Compound 14

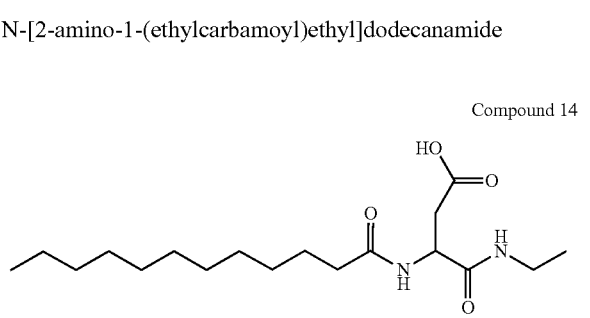

Compound 16

2-dodecanamido-3-(ethylamino)-3-oxopropyl dihydrogen phosphate

Compound 17

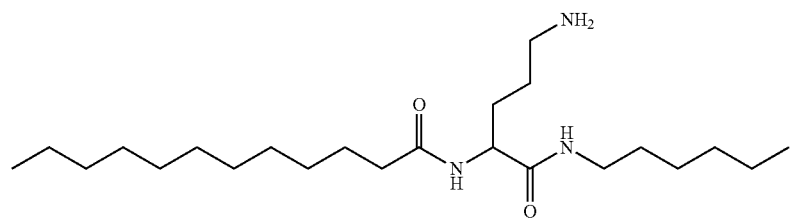

N-(5-amino-1-(hexylamino)-1-oxopentan-2-yl)dodecanamide

Compound 18

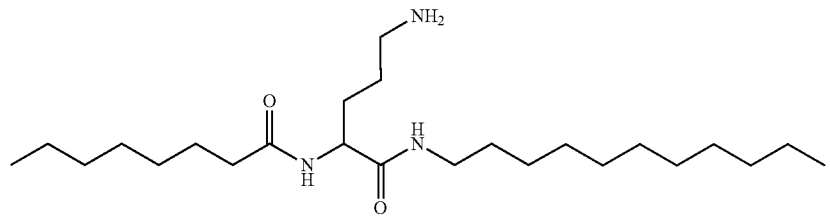

| 11 | 12 |
|---|---|
| N-(5-amino-1-oxo-1-(undecylamino)pentan-2-yl)octanamide | N-(1-(ethylamino)-5-guanidino-1-oxopentan-2-yl)tetradecanamide |
Compound 19
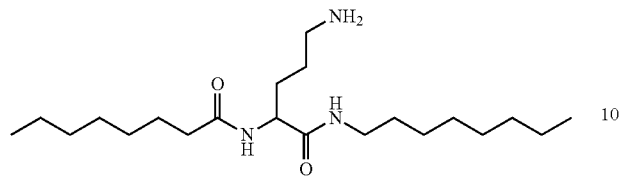
N-(5-amino-1-(octylamino)-1-oxopentan-2-yl)octanamide
Compound 20
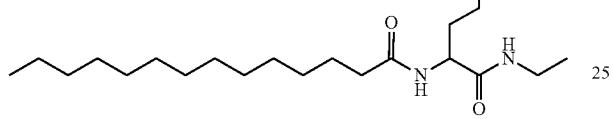
Compound 21
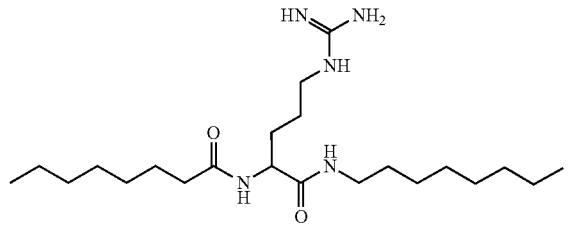
N-(5-guanidino-1-(octylamino)-1-oxopentan-2-yl)octanamide
Compound 22
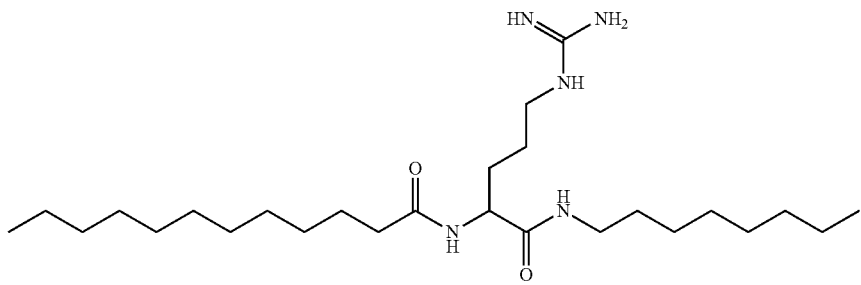
N-(5-guanidino-1-(octylamino)-1-oxopentan-2-yl)dodecanamide
Compound 23
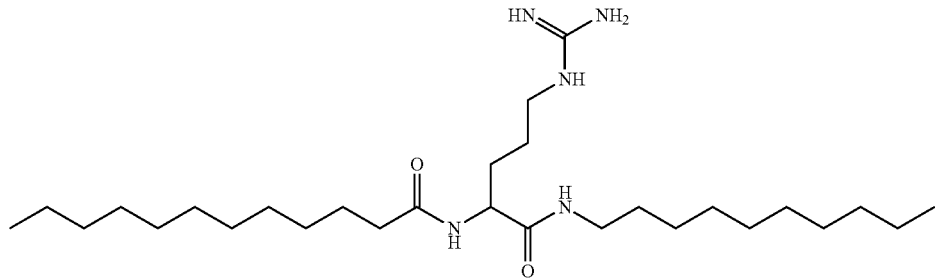

N-(1-(decylamino)-5-guanidino-1-oxopentan-2-yl)dodecanamide

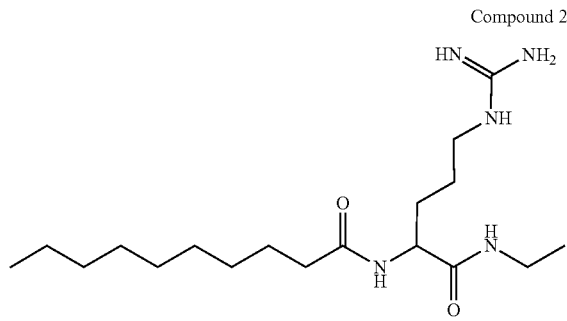

Compound 24

N-(1-(ethylamino)-5-guanidino-1-oxopentan-2-yl)decanamide

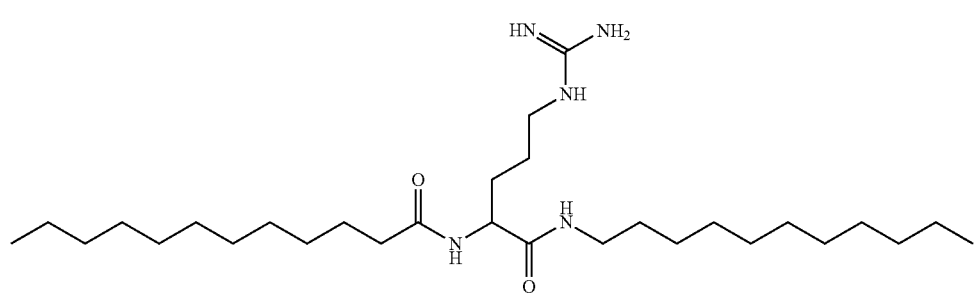

Compound 25

N-(5-guanidino-1-oxo-1-(undecylamino)pentan-2-yl)dodecanamide

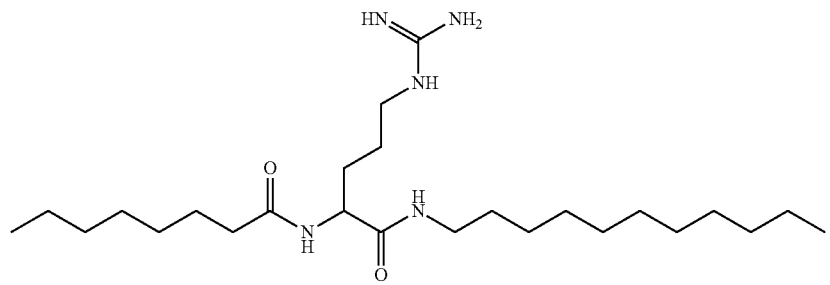

Compound 26

N-(5-guanidino-1-oxo-1-(undecylamino)pentan-2-yl)octanamide

Any of a variety of suitable methods for synthesizing the compounds of the present invention may be used. For example, on particular method for synthesizing [amino({[4-dodecanamido-4-(ethylcarbamoyl)butyl]amino})methylidene]azanium is described in Example 1. As will be recognized by those of skill in the art, other similar compounds of Formula I may be synthesized in a similar manner using the appropriate starting materials to achieve the appropriate $R_1$, $R_2$, $R_3$ and n substitution on the molecule without undue experimentation.

Applicants have recognized that the compounds of the present invention provide a wide variety of benefits, including, for example, in compositions for use in healthcare applications. Accordingly, in certain embodiments, the present invention is directed to healthcare compositions comprising at least one compound of Formula I. Such healthcare compositions may be in any suitable form for use as, in, or on personal care, cosmetic, pharmaceutical, and medical device products, and the like. In certain preferred embodiments, the compositions of the present invention are compositions for oral care, including, for example, oral care compositions in the form of a solution, mouthwash, mouth rinse, mouth spray, toothpaste, tooth gel, sub-gingival gel, mousse, foam, denture care product, dentifrice, lozenge, chewable tablet, dissolvable tablet, dry powder and the like. The oral care composition may also be incorporated into or onto floss, dissolvable strips or films or integrated into or onto a device or applicator for oral use.

In certain embodiments, the compositions of the invention comprise at least one composition of Formula I and a vehicle. Any suitable vehicle may be used in the compositions of the present invention. Preferably, the vehicle is selected from the group consisting of cosmetically-acceptable and pharmaceutically-acceptable vehicles. As used herein, "cosmetically-acceptable" and "pharmaceutically-acceptable" vehicles are liquid, solid, or other ingredients suitable for use as vehicles in products for mammals, including humans without undue toxicity, incompatibility, instability, irritation, allergic response, and the like.

For liquid compositions, the vehicle may be any suitable aqueous or non-aqueous liquid vehicle. In certain embodiments, the liquid vehicle comprises water. For example, in many compositions, as will be understood by those of skill in the art, water is added to q.s. (Quantum Sufficit, Latin for "as much as needed") the composition. In certain embodiments, the composition comprises from about 60% to about 99.99% water, including from about 70% to about 95% water, from about 80% to 95% water, from about 60% to about 90% water, from about 60% to about 80% water, or from about 60% to about 75% water.

In certain embodiments, alcohol may be added to the composition. Any of a variety of alcohols represented by the formula $R_4$—OH, wherein $R_4$ is an alkyl group having from 2 to 6 carbons, may be used in the present invention. Examples of suitable alcohols of formula $R_4$—OH include ethanol; n-propanol, iso-propanol; butanols; pentanols; hexanols, and combinations of two or more thereof, and the like. In certain embodiments, the alcohol is, or comprises, ethanol. In some embodiments, the alcohol may be present in the composition in an amount of at least about 10.0% v/v of the total composition, or from about 10% to about 35% v/v of the total composition, or from about 15% to about 30% v/v of the total composition and may be from about 20% to about 25% v/v of the total composition.

Applicants have discovered that the compounds of the present invention exhibit increased stability in low-alcohol or alcohol-free formulations, while maintaining other oral care benefits, as compared to previously known amino acid derivative compounds. Accordingly, in some embodiments, the composition may comprise a reduced level of alcohol. The phrase "reduced level" of alcohol means an amount of a $R_4$—OH alcohol of about 10% v/v or less, optionally of about 5% v/v or less, optionally of about 1% v/v or less, optionally of about 0.1% v/v or less by volume of the total composition. In certain embodiments, the compositions of the present invention are free of $R_4$—OH alcohols.

Alternatively, the compositions of the present invention may be formulated in a dissolvable tablet, dry powder, chewing gum, film, semi-solid, solid, or liquid concentrate form. In such embodiments, for example, water is added to q.s. as necessary in the case of liquid dissolvable tablet, concentrates or powdered formulations, or water may be removed using standard evaporation procedures known in the art to produce a composition in dry powder form. Evaporated, or freeze-dried forms are advantageous for storage and shipping.

Any suitable amounts of one or more compounds of Formula I may be used in the compositions of the present invention. In certain embodiments, the compositions comprise a total amount of compounds of Formula I (whether the composition comprises only one compound of Formula I or a combination of two or more thereof) of about 0.0001% to about 50% w/w of active/solid amount of total compounds of Formula I based on the total weight of the composition. In certain embodiments, the percent of total compound(s) of Formula I is from about 0.001% to about 10%, or from about 0.01% to about 1%, or from about 0.05% to about 0.5% w/w of active/solid amount of total compounds of Formula I based on the total weight of the composition.

In certain embodiments, as will be recognized by those of skill in the art, compounds made in accord with the present invention may be purified and/or may comprise a mixture of two or more compounds of Formula I. In certain embodiments, the compositions of the present invention comprise a combination of at least two compounds of Formula I. In certain embodiments, the compositions of the present invention comprise a combination of at least three compounds of Formula I.

The compositions of the present invention may further comprise any of a variety of optional ingredients therein, including, but not limited to oily components, active ingredients, additional surfactants, humectants, solvents, flavors, sweeteners, colorants, preservatives, pH adjusters, pH buffers, and the like.

Any of a variety of oily components may be used in the present compositions. The oily component may comprise any one or more oils, or other materials that are water insoluble, or substantially water-insoluble, meaning that its solubility is less than about 1% by weight in water at 25° C. or, optionally, less than about 0.1%. In certain embodiments, the oily component of the present invention comprises, consists essentially of, or consists of, at least one essential oil, i.e., a natural or synthetic (or combination thereof) concentrated hydrophobic material of vegetable origin, generally containing volatile compounds, at least one flavor oil, or a combination of two or more thereof. Examples of suitable essential oils, flavor oils, and their amounts are described below. In certain embodiments, the composition comprises a total amount of oily component of about 0.05% w/w or more, about 0.1% w/w or more, or about 0.2% w/w or more of oily component.

In certain embodiments, compositions of the present invention comprise essential oils. Essential oils are volatile aromatic oils which may be synthetic or may be derived from plants by distillation, expression or extraction, and which usually carry the odor or flavor of the plant from which they are obtained. Useful essential oils may provide antiseptic activity. Some of these essential oils also act as flavoring agents. Useful essential oils include but are not limited to citra, thymol, menthol, methyl salicylate (wintergreen oil), eucalyptol, carvacrol, camphor, anethole, carvone, eugenol, isoeugenol, limonene, osimen, n-decyl alcohol, citronel, α-salpineol, methyl acetate, citronellyl acetate, methyl eugenol, cineol, linalool, ethyl linalaol, safrola vanillin, spearmint oil, peppermint oil, lemon oil, orange oil, sage oil, rosemary oil, cinnamon oil, pimento oil, laurel oil, cedar leaf oil, gerianol, verbenone, anise oil, bay oil, benzaldehyde, bergamot oil, bitter almond, chlorothymol, cinnamic aldehyde, citronella oil, clove oil, coal tar, eucalyptus oil, guaiacol, tropolone derivatives such as hinokitiol, lavender oil, mustard oil, phenol, phenyl salicylate, pine oil, pine needle oil, sassafras oil, spike lavender oil, storax, thyme oil, tolu balsam, turpentine oil, clove oil, and combinations thereof.

In certain embodiments, the essential oils are selected from the group consisting of thymol ($(CH_3)_2CHC_6H_3(CH_3)$OH, also known as isopropyl-m-cresol), eucalyptol ($C_{10}H_{18}O$, also known as cineol), menthol ($CH_3C_6H_9(C_3H_7)OH$), also known as hexahydrothymol), methyl salicylate ($C_6H_4OHCOOCH_3$, also known as wintergreen oil), isomers of each of these compounds, and combinations of two or more thereof. In some embodiments, the compositions of the present invention contain thymol. In some embodiments, the compositions of the present invention contain menthol. In some embodiments, the composition contains all four of these essential oils.

In certain embodiments, thymol is employed in amounts of from about 0.0001% to about 0.6% w/v, or from about 0.005% to about 0.07% w/v of the composition. In certain embodiments, eucalyptol may be employed in amounts of from about 0.0001% to about 0.51 w/v, or from about 0.0085% to about 0.10% w/v of the composition. In certain embodiments, menthol is employed in amounts of from about 0.0001% to about 0.25% w/v, or from about 0.0035% to about 0.05% w/v of the composition. In certain embodiments, methyl salicylate is employed in amounts of from about 0.0001% to about 0.28% w/v, or from about 0.004% to about 0.07% w/v of the composition. In certain embodiments, the total amount of all of such essential oils present in the disclosed compositions can be from about 0.0004% to about 1.64% w/v, or from about 0.0165% to about 0.49% w/v of the composition.

In certain embodiments, fluoride providing compounds may be present in the mouth rinse compositions of this invention. These compounds may be slightly water soluble or may be fully water soluble and are characterized by their ability to release fluoride ions or fluoride containing ions in water. Typical fluoride providing compounds are inorganic fluoride salts such as soluble alkali metal, alkaline earth metal, and heavy metal salts, for example, sodium fluoride, potassium fluoride, ammonium fluoride, cupric fluoride, zinc fluoride, stannic fluoride, stannous fluoride, barium fluoride, sodium hexafluorosilicate, ammonium hexafluorosilicate, sodium fluorozirconate, sodium monofluorophosphate, aluminum mono- and difluorophosphate and fluorinated sodium calcium pyrophosphate. Amine fluorides, such as N'-octadecyltrimethylendiamine-N,N,N'-tris(2-ethanol)-dihydrofluoride and 9-octadecenylamine-hydrofluoride), may also be used. In certain embodiments, the fluoride providing compound is generally present in an amount sufficient to release up to about 5%, or from about 0.001% to about 2%, or from about 0.005% to about 1.5% fluoride by weight of the composition.

In certain embodiments, sensitivity reducing agents, such as potassium salts of nitrate and oxalate in an amount from about 0.1% to about 5.0% w/v of the composition may be incorporated into the present invention. Other potassium releasing compounds are feasible (e.g., KCl). High concentrations of calcium phosphates may also provide some added sensitivity relief. These agents are believed to work by either forming an occlusive surface mineral deposit on the tooth surface or through providing potassium to the nerves within the teeth to depolarize the nerves. A more detailed discussion of suitable sensitivity reducing agents can be found in US 2006/0013778 to Hodosh and U.S. Pat. No. 6,416,745 to Markowitz et al., both of which are herein incorporated by reference in their entirety.

In certain embodiments, compounds with anti-calculus benefits (e.g., various carboxylates, polyaspartic acid, etc.) may be incorporated into the present invention. Also useful as an anticalculus agent are the anionic polymeric polycarboxylates. Such materials are well known in the art, being employed in the form of their free acids or partially or preferably fully neutralized water-soluble alkali metal (e.g., potassium and preferably sodium) or ammonium salts. Preferred are 1:4 to 4:1 by weight copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available, for example, as Gantrez 25 AN 139 (M.W. 500,000), AN 119 (M.W. 250,000) and preferably S-97 Pharmaceutical Grade (M.W. 70,000), of GAF Chemicals Corporation.

Additional anti-calculus agents may be selected from the group consisting of polyphosphates (including pyrophosphates) and salts thereof polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof; carboxy-substituted polymers; and mixtures thereof. In one embodiment, the salts are alkali metal or ammonium salts. Polyphosphates are generally employed as their wholly or partially neutralized water-soluble alkali metal salts such as potassium, sodium, ammonium salts, and mixtures thereof. The inorganic polyphosphate salts include alkali metal (e.g., sodium) tripolyphosphate, tetrapolyphosphate, dialkyl metal (e.g., disodium) diacid, trialkyl metal (e.g., trisodium) monoacid, potassium hydrogen phosphate, sodium hydrogen phosphate, and alkali metal (e.g., sodium) hexametaphosphate, and mixtures thereof. Polyphosphates larger than tetrapolyphosphate usually occur as amorphous glassy materials. In one embodiment the polyphosphates are those manufactured by FMC Corporation, which are commercially known as Sodaphos (n≈6), Hexaphos (n≈13), and Glass H (n≈21, sodium hexametaphosphate), and mixtures thereof. The pyrophosphate salts useful in the present invention include, alkali metal pyrophosphates, di-, tri-, and mono-potassium or sodium pyrophosphates, dialkali metal pyrophosphate salts, tetraalkali metal pyrophosphate salts, and mixtures thereof. In one embodiment the pyrophosphate salt is selected from the group consisting of trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof. Polyolefin sulfonates include those wherein the olefin group contains 2 or more carbon atoms, and salts thereof. Polyolefin phosphonates include those wherein the olefin group contains 2 or more carbon atoms. Polyvinylphosphonates include polyvinylphosphonic acid. Diphosphonates and salts thereof include azocycloalkane-2,2-diphosphonic acids and salts thereof, ions of azocycloalkane-2,2-diphosphonic acids and salts thereof, azacyclohexane-2,2-diphosphonic acid, azacyclopentane-2,2-diphosphonic acid, N-methyl-azacyclopentane-2,3-diphosphonic acid, EHDP (ethane-1-hydroxy-1,1-diphosphonic acid), AHP (azacycloheptane-2,2-diphosphonic acid), ethane-1-amino-1,1-diphosphonate, dichloromethane-diphosphonate, etc. Phosphonoalkane carboxylic acid or their alkali metal salts include PPTA (phosphonopropane tricarboxylic acid), PBTA (phosphonobutane-1,2,4-tricarboxylic acid), each as acid or alkali metal salts. Polyolefin phosphates include those wherein the olefin group contains 2 or more carbon atoms. Polypeptides include polyaspartic and polyglutamic acids.

In certain embodiments, zinc salts such as zinc chloride, zinc acetate or zinc citrate may be added as an astringent for an "antiseptic cleaning" feeling, as a breath protection enhancer or as anti-calculus agent in an amount of from about 0.0025% w/v to about 0.75% w/v of the composition.

Any of a variety of additional surfactants may be used in the present invention. Suitable surfactants may include anionic, non-ionic, cationic, amphoteric, zwitterionic surfactants, and combinations of two or more thereof. Examples of suitable surfactants are disclosed, for example, in U.S. Pat. No. 7,417,020 to Fevola, et al which is incorporated in its entirety herein by reference.

In certain embodiments, the compositions of the present invention comprise a non-ionic surfactant. Those of skill in the art will recognize that any of a variety of one or more non-ionic surfactants include, but are not limited to, compounds produced by the condensation of alkylene oxide groups (hydrophilic in nature) with an organic hydrophobic compound which may be aliphatic or alkyl-aromatic in nature. Examples of suitable nonionic surfactants include, but are not limited to, alkyl polyglucosides; alkyl glucose amines, block copolymers such as ethylene oxide and propylene oxide copolymers e.g. Poloxamers; ethoxylated hydrogenated castor oils available commercially for example under the trade name CRODURET (Croda Inc., Edison, N.J.); alkyl polyethylene oxide e.g. Polysorbates, and/or; fatty alcohol ethoxylates; polyethylene oxide condensates of alkyl phenols; products derived from the condensation of ethylene oxide with the reaction product of propylene oxide and ethylene diamine; ethylene oxide condensates of aliphatic alcohols; long chain tertiary amine oxides; long chain tertiary phosphine oxides; long chain dialkyl sulfoxides; and mixtures thereof.

Exemplary non-ionic surfactants are selected from the group known as poly(oxyethylene)-poly(oxypropylene) block copolymers. Such copolymers are known commercially as poloxamers and are produced in a wide range of structures and molecular weights with varying contents of ethylene oxide. These non-ionic poloxamers are non-toxic and acceptable as direct food additives. They are stable and readily dispersible in aqueous systems and are compatible with a wide variety of formulations and other ingredients for oral preparations. These surfactants should have an HLB (Hydrophilic-Lipophilic Balance) of between about 10 and about 30 and preferably between about 10 and about 25. By way of example, non-ionic surfactants useful in this invention include the poloxamers identified as poloxamers 105, 108, 124, 184, 185, 188, 215, 217, 234, 235, 237, 238, 284, 288, 333, 334, 335, 338, 407, and combinations of two or more thereof. In certain preferred embodiments, the composition comprises poloxamer 407.

In certain embodiments, the compositions of the claimed invention comprise less than about 9% of non-ionic surfactant, less than 5%, or less than 1.5%, or less than 1%, or less than 0.8, less than 0.5%, less than 0.4%, or less than 0.3% of non-ionic surfactants. In certain embodiments, the composition of the present invention is free of non-ionic surfactants.

In certain embodiments, the compositions of the present invention also contain at least one alkyl sulfate surfactant. In certain embodiments, suitable alkyl sulfate surfactants include, but are not limited to sulfated $C_8$ to $C_{18}$, optionally sulfated $C_{10}$ to $C_{16}$ even numbered carbon chain length alcohols neutralized with a suitable basic salt such as sodium carbonate or sodium hydroxide and mixtures thereof such that the alkyl sulfate surfactant has an even numbered $C_8$ to $C_{18}$, optionally $C_{10}$ to $C_{16}$, chain length. In certain embodiments, the alkyl sulfate is selected from the group consisting of sodium lauryl sulfate, hexadecyl sulfate and mixtures thereof. In certain embodiments, commercially available mixtures of alkyl sulfates are used. A typical percentage breakdown of alkyl sulfates by alkyl chain length in commercially available sodium lauryl sulfate (SLS) is as follows:
Alkyl Component
Chain Percentage
Length in SLS
$C_{12}$ >60%
$C_{14}$ 20%-35%
$C_{16}$ <10%
$C_{10}$ <1%
$C_{18}$ <1%

In certain embodiments, the alkyl sulfate surfactant is present in the composition from about 0.001% to about 6.0% w/v, or optionally from about 0.1% to about 0.5% w/v of the composition.

Another suitable surfactant is one selected from the group consisting of sarcosinate surfactants, isethionate surfactants and taurate surfactants. Preferred for use herein are alkali metal or ammonium salts of these surfactants, such as the sodium and potassium salts of the following: lauroyl sarcosinate, myristoyl sarcosinate, palmitoyl sarcosinate, stearoyl sarcosinate and oleoyl sarcosinate. The sarcosinate surfactant may be present in the compositions of the present invention from about 0.1% to about 2.5%, or from about 0.5% to about 2% by weight of the total composition.

Zwitterionic synthetic surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

The amphoteric surfactants useful in the present invention include, but are not limited to, derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Examples of suitable amphoteric surfactants include, but are not limited alkylimino-diproprionates, alky lamphoglycinates (mono or di), alkylamphoproprionates (mono or di), alkylamphoacetates (mono or di), N-alkyl [3-aminoproprionic acids, alkylpolyamino carboxylates, phosphorylated imidazolines, alkyl betaines, alkylamido betaines, alkylamidopropyl betaines, alkyl sultaines, alkylamido sultaines, and mixtures thereof. In certain embodiments, the amphoteric surfactant is selected from the group consisting of alkylamidopropyl betaines, amphoacetates such as sodium auroamphoacetate and mixtures thereof. Mixtures of any of the above-mentioned surfactants can also be employed. A more detailed discussion of anionic, nonionic, and amphoteric surfactants can be found in U.S. Pat. No. 7,087,650 to Lennon; U.S. Pat. No. 7,084,104 to Martin et al.; U.S. Pat. No. 5,190,747 to Sekiguchi et al.; and U.S. Pat. No. 4,051,234, Gieske, et al., each of which patents are herein incorporated by reference in their entirety.

In certain embodiments, the compositions of the claimed invention comprise less than about 9% of amphoteric surfactant, less than 5%, or less than 1.5%, or less than 1%, or less than 0.8, less than 0.5%, less than 0.4%, or less than 0.3% of amphoteric surfactants. In certain embodiments, the composition of the present invention is free of amphoteric surfactants.

Additional surfactants may be added with the alkyl sulfate surfactant to aid in solubilization of the essential oils provided such surfactants do not affect the bioavailability of the essential oils. Suitable examples include additional anionic surfactants, nonionic surfactants, amphoteric surfactants and mixtures thereof. However, in certain embodiments, the total surfactant concentration (including the alkyl sulfate surfactant alone or in combination with other surfactants) for mouth rinses of the present invention should not exceed or should about 9% or less, optionally, the total surfactant concentration should be about 5% or less, optionally about 1% or less, optionally about 0.5% or less w/w % of active surfactant by weight of the composition.

In certain embodiments, a sugar alcohol (humectant) is also added to the oral compositions of the present invention. The sugar alcohol solvent(s) may be selected from those multi-hydroxy-functional compounds that are conventionally used in oral and ingestible products. In certain embodiments, the sugar alcohol (s) should be nonmetabolized and non-fermentable sugar alcohol (s). In specific embodiments, the sugar alcohols include, but are not limited to sorbitol, glycerol, xylitol, mannitol, maltitol, inositol, allitol, altritol, dulcitol, galactitol, glucitol, hexitol, iditol, pentitol, ribitol, erythritol and mixtures thereof. Optionally, the sugar alcohol is selected from the group consisting of sorbitol and xylitol or mixtures thereof. In some embodiments, the sugar alcohol is sorbitol. In certain embodiments, the total amount of sugar alcohol (s), which are added to effectively aid in the dispersion or dissolution of the mouth rinse or other ingredients, should not exceed about 50% w/ of the total composition. Or, total amount of sugar alcohol should not exceed about 30% w/v of the total composition. Or, total amount of sugar alcohol should not exceed 25% w/v of the total composition. The sugar alcohol can be in an amount of from about 1.0% to about 24% w/v, or from about 1.5% to about 22% w/v, or from about 2.5% to about 20% w/v of the total composition.

In certain embodiments, a polyol solvent is added to the composition. The polyol solvent comprises a polyol or polyhydric alcohol selected from the group consisting of polyhydric alkanes (such as propylene glycol, glycerin, butylene glycol, hexylene glycol, 1,3-propanediol); polyhydric alkane esters (dipropylene glycol, ethoxydiglycol); polyalkene glycols (such as polyethylene glycol, polypropylene glycol) and mixtures thereof. In certain embodiments, the polyol solvent can be present in an amount of from 0% to about 40% w/v, or from about 0.5% to about 20% w/v, or from about 1.0% to about 10% w/v of the composition.

In certain embodiments, the compositions of the present invention have a pH of about 11 or less. In some embodiments, the compositions have a pH of from about 3 to about 7, or from about 3.5 to about 6.5, or from about 3.5 to about 5.0.

As will be recognized by those of skill in the art, the pH of the composition may be adjusted or maintained using a buffer in an amount effective to provide the composition with a pH at or below 11. The composition can optionally comprise at least one pH modifying agents among those useful herein include acidifying agents to lower pH, basifying agents to raise pH, and buffering agents to maintain pH within a desired range. For example, one or more compounds selected from acidifying, basifying and buffering agents can be included to provide a pH of about 2 to about 7, or in various embodiments from about 3 to about 6, or from about 4 to about 5. Any orally acceptable pH modifying agent can be used including without limitation hydrochloric, carboxylic, and sulfonic acids, acid salts (e.g., monosodium citrate, disodium citrate, monosodium malate, etc.), alkali metal hydroxides such as sodium hydroxide, borates, silicates, imidazole and mixtures thereof. One or more pH modifying agents are optionally present in a total amount effective to maintain the composition in an orally acceptable pH range. In certain embodiments, inorganic acids may be used as the buffer added to the composition.

In certain embodiments, organic acids may be used as the buffer added to the composition. Organic acids suitable for use in the compositions of the present invention include, but are not limited to, ascorbic acid, sorbic acid, citric acid, glycolic acid, lactic acid and acetic acid, benzoic acid, salicylic acid, phthalic acid, phenolsulphonic acid, and mixtures thereof, optionally, the organic acid is selected from the group consisting of benzoic acid, sorbic acid, citric acid, and mixtures thereof, or optionally, the organic acid is benzoic acid.

Generally, the amount of buffering compound is from about 0.001% to about 20.0% of the composition. In certain embodiment, the organic acid buffer is present in amounts of from about 0.001% to about 10% w/v of the composition, or from about 0.01% to about 1% of the composition.

In certain embodiments, additional conventional components may be added as in mouthwashes and mouth rinses of the prior art. Whereas some alcohol containing mouth rinses have a pH of about 7.0, reduction of the alcohol level may require the addition of acidic preservatives, such as sorbic acid or benzoic acid, which reduce pH levels. Buffer systems are then necessary to control the pH of the composition at optimal levels. This is generally accomplished through the addition of a weak acid and its salt or a weak base and its salt. In some embodiments, useful systems have been found to be sodium benzoate and benzoic acid in amounts of from 0.01% (or about 0.01% w/v) to 1.0% w/v (or about 1.0% w/v) of the composition, and sodium citrate and citric acid in amounts of from 0.001% (or about 0.001% w/v) to 1.0% w/v (or about 1.0% w/v) of the composition, phosphoric acid, and sodium/potassium phosphate of amounts from 0.01% (or about 0.01%) to 1.0% (or about 1.0%) by weight of the composition. In certain embodiments, the buffers are incorporated in amounts that maintain the pH at levels of from 3.0 (or about 3.0) to 8.0 (or about 8.0), optionally from 3.5 (or about 3.5) to 6.5 (or about 6.5), optionally from 3.5 (or about 3.5) to 5.0 (or about 5.0).

Additional buffering agents include alkali metal hydroxides, ammonium hydroxide, organic ammonium compounds, carbonates, sesquicarbonates, borates, silicates, phosphates, imidazole, and mixtures thereof. Specific buffering agents include monosodium phosphate, trisodium phosphate, sodium hydroxide, potassium hydroxide, alkali metal carbonate salts, sodium carbonate, imidazole, pyrophosphate salts, sodium gluconate, sodium lactate, citric acid, and sodium citrate.

Sweeteners such as aspartame, sodium saccharin (saccharin), sucralose, *stevia*, acesulfame K and the like may be added for better taste in amounts of from about 0.0001% w/v to about 1.0% w/v. In certain preferred embodiments, the sweetener comprises sucralose.

In certain embodiments, the composition further comprises flavors or flavorants to modify or magnify the taste of the composition or reduce or mask the sharp "bite" or "burn" of ingredients such as thymol. Suitable flavors include, but are not limited to, flavor oils such as oil of anise, anethole, benzyl alcohol, spearmint oil, citrus oils, vanillin, and the like may be incorporated. Other flavors such as citrus oils, vanillin and the like may be incorporated to provide further taste variations. In these embodiments, the amount of flavor oil added to the composition can be from about 0.001% to about 5% w/v, or from about 0.01% to about 0.3% w/v of the total composition. The flavors or flavorants, and other taste improving ingredients, employed will vary depending upon the particular taste and feel desired. Those skilled in the art can select and customize these types of ingredients to provide the desired results.

In certain embodiments, acceptably approved food dyes may be used to provide a pleasing color to the compositions of the invention. These may be selected from, but not limited to, the long list of acceptable food dyes. Suitable dyes for this purpose include FD&C yellow #5, FD&C yellow #10, FD&C blue #1 and FD&C green #3. These are added in conventional amounts, typically in individual amounts of from about 0.00001% w/v to about 0.0008% w/v, or from about 0.000035% w/v to about 0.0005% w/v of the composition.

Other conventional ingredients may be used in the liquid or mouth rinse compositions of this invention, including those known and used in the art. Examples of such ingredients include thickeners, suspending agents and softeners. Thickeners and suspending agents useful in the compositions of the present invention can be found in U.S. Pat. No. 5,328,682 to Pullen et al., herein incorporated by reference in its entirety. In certain embodiments, these are incorporated in amounts of from about 0.1% w/v to about 0.6% w/v, or about 0.5% w/v of the composition.

In some embodiments, antimicrobial preservatives may be added to the composition. Some antimicrobial preservatives which may be used include, but are not limited to cationic antibacterials, such as sodium benzoate, polyquaternium polycationic polymers (i.e., polyquaternium-42: Poly[oxyethylene(dimethylimino)ethylene (dimethylimino)ethylene dichloride]), quaternary ammonium salts or quaternary ammonium compounds, parabens (i.e. parahydroxybenzoates or esters of parahydroxybenzoic acid), hydroxyacetophenone, 1,2-Hexanediol, Caprylyl Glycol, chlorhexidine, alexidine, hexetidine, benzalkonium chloride, domiphen bromide, cetylpyridinium chloride (CPC), tetradecylpyridinium chloride (TPC), N-tetradecyl-4-ethylpyridinium chloride (TDEPC), octenidine, bisbiguanides, zinc or stannous ion agents, grapefruit extract, and mixtures thereof. Other antibacterial and antimicrobial agents include, but are not limited to: 5-chloro-2-(2,4-dichlorophenoxy)-phenol, commonly referred to as triclosan; 8-hydroxyquinoline and its salts, copper II compounds, including, but not limited to, copper(II) chloride, copper(II) sulfate, copper(II) acetate, copper(II) fluoride and copper(II) hydroxide; phthalic acid and its salts including, but not limited to those disclosed in U.S. Pat. No. 4,994,262, including magnesium monopotassium phthalate; sanguinarine; salicylanilide; iodine; sulfonamides; phenolics; delmopinol, octapinol, and other piperidino derivatives; niacin preparations; nystatin; apple extract; thyme oil; thymol; antibiotics such as augmentin, amoxicillin, tetracycline, doxycycline, minocycline, metronidazole, neomycin, kanamycin, cetylpyridinium chloride, and clindamycin; analogs and salts of the above; methyl salicylate; hydrogen peroxide; metal salts of chlorite; pyrrolidone ethyl cocoyl arginate; lauroyl ethyl arginate monochlorohydrate; and mixtures of all of the above. In another embodiment, the composition comprises phenolic antimicrobial compounds and mixtures thereof. Antimicrobial components may be present from about 0.001% to about 20% by weight of the oral care composition. In another embodiment the antimicrobial agents generally comprise from about 0.1% to about 5% by weight of the oral care compositions of the present invention.

Other antibacterial agents may be basic amino acids and salts. Other embodiments may comprise arginine.

Other useful oral care actives and/or inactive ingredients and further examples thereof can be found in U.S. Pat. No. 6,682,722 to Majeti et al. and U.S. Pat. No. 6,121,315 to Nair et al., each of which are herein incorporated by reference in its entirety.

The compositions of the present invention may be made according to any of a variety of methods disclosed herein and known in the art. In particular, applicants have discovered for certain oral care compositions, that the present compounds may be incorporated into oral care compositions to produce compositions that tend to be relatively more stable than prior compositions, including, for example, similar compositions comprising LAE.

According to certain embodiments, the compositions of the present invention may be made according to the following method(s).

The compounds and compositions of the present invention may be used in a variety of methods of treating a mammalian body. Such methods generally comprise introducing a compound or composition of the present invention into or onto the mammalian body to be treated. For example, certain methods of the present invention comprise treating a condition or disease of the skin, mucosal membrane, hair, eye, or other part of the mammalian body by applying to the skin, mucosal membrane, hair, eye, or other part of the body, respectively, or injecting into the mammalian body, a compound or composition of the claimed invention. Certain methods of the present invention comprise treating a condition or disease of the oral cavity, including the teeth, mucosal membranes/gums, and the like, by applying to the oral cavity, or injecting into the oral cavity or otherwise into the mammalian body, a compound or composition of the claimed invention.

The compounds and compositions of the present invention may be used in a variety of methods of treating a mammalian body, in particular for disrupting a biofilm on a surface of the oral cavity. According to certain embodiments, the present invention comprises disrupting biofilm on a surface by contacting the surface comprising biofilm with a composition of the present invention. In certain embodiments, the present invention comprises removing biofilm from a surface by contacting the surface comprising biofilm with a composition of the present invention. In certain embodiments, the present invention comprises reducing bacterial attachment to a surface by contacting the surface with a composition of the present invention. In certain embodiments, the present method comprises inhibiting plaque by contacting a surface of the oral cavity with a compound or composition of the present invention.

Any suitable surface of the oral cavity may be contacting in accord with the methods of the present invention including one or more surfaces selected from the group consisting of surfaces of one or more teeth, surfaces of the gums, combinations of two or more thereof, and the like.

In each of the above methods, the composition of the claimed method may be introduced to the surface to be contacted via any of a variety of methods. In certain embodiments, the composition is introduced into the oral cavity and applied to the surface by a user as a mouthwash or mouth rinse. In certain embodiments, the composition is introduced to the oral cavity and applied to the surface as a toothpaste on an article for cleaning the teeth, e.g., a toothbrush. The compositions of the present invention may be further introduced via the mouth and applied to the surface as a gum, lozenge, dissolvable strip, or the like.

Furthermore, the contacting step of the methods of the present invention may comprise contacting the surface with the composition for any suitable amount of time. In certain embodiments, the contacting step comprises contacting the surface for less than thirty seconds. In certain embodiments, the contacting step comprises contacting the surface with the composition for thirty seconds or more, for example, for about thirty seconds, for about 40 seconds, for about one minute, or for greater than one minute.

EXAMPLES

Example 1: Synthesis of [amino({[4-dodecanamido-4-(ethylcarbamoyl)butyl]amino})methylidene]azanium (compound 9)

Reaction scheme employed for the synthesis of compound 9

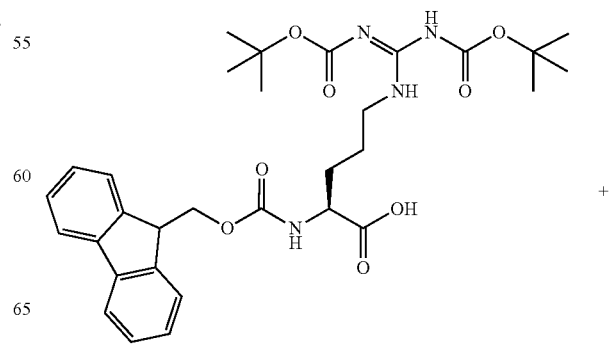

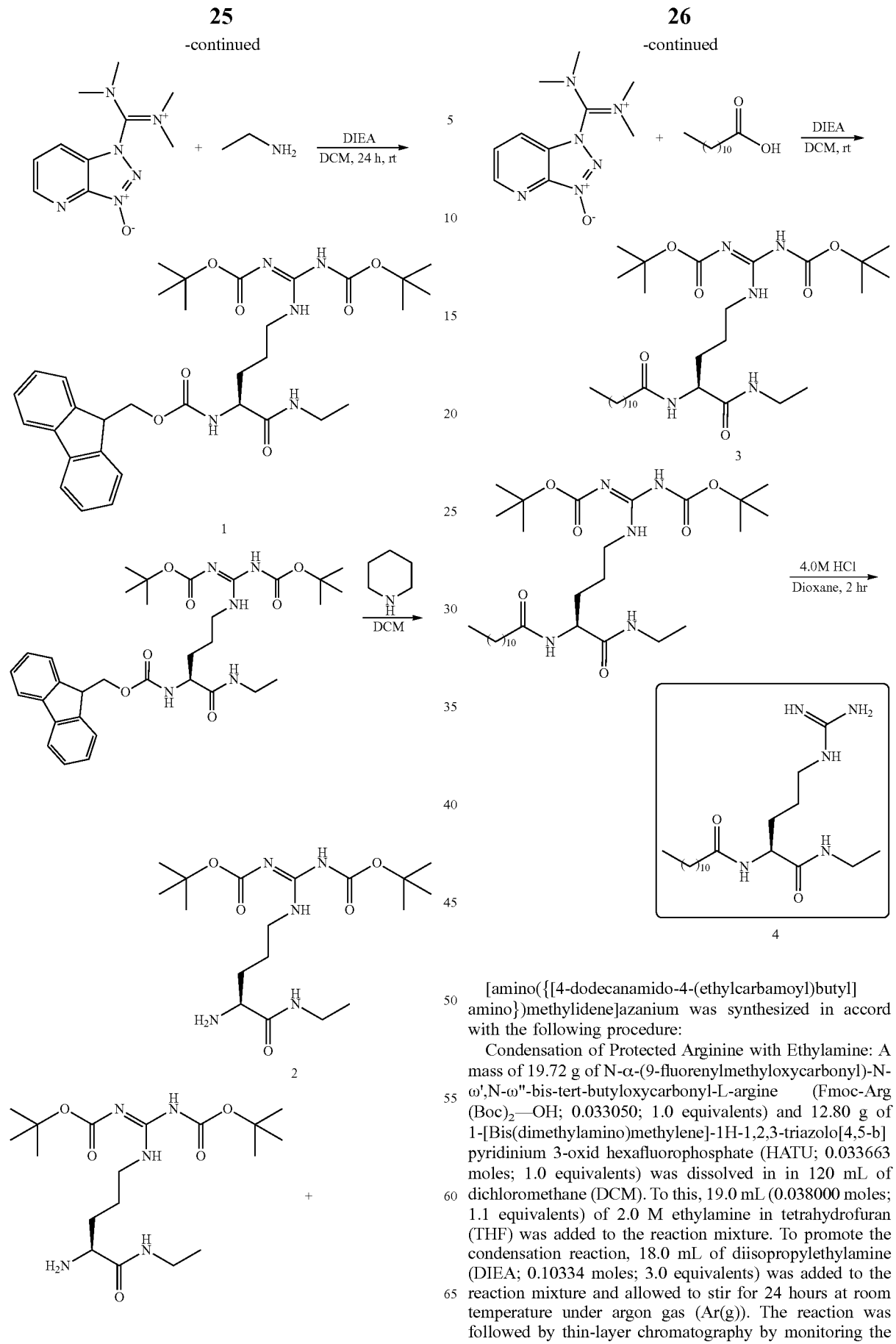

[amino({[4-dodecanamido-4-(ethylcarbamoyl)butyl]amino})methylidene]azanium was synthesized in accord with the following procedure:

Condensation of Protected Arginine with Ethylamine: A mass of 19.72 g of N-α-(9-fluorenylmethyloxycarbonyl)-N-ω',N-ω"-bis-tert-butyloxycarbonyl-L-argine (Fmoc-Arg(Boc)$_2$—OH; 0.033050; 1.0 equivalents) and 12.80 g of 1-[Bis(dimethylamino)methylene]-1H-1,2,3-triazolo[4,5-b]pyridinium 3-oxid hexafluorophosphate (HATU; 0.033663 moles; 1.0 equivalents) was dissolved in in 120 mL of dichloromethane (DCM). To this, 19.0 mL (0.038000 moles; 1.1 equivalents) of 2.0 M ethylamine in tetrahydrofuran (THF) was added to the reaction mixture. To promote the condensation reaction, 18.0 mL of diisopropylethylamine (DIEA; 0.10334 moles; 3.0 equivalents) was added to the reaction mixture and allowed to stir for 24 hours at room temperature under argon gas (Ar(g)). The reaction was followed by thin-layer chromatography by monitoring the consumption of reactants and production of product 1. Upon completion, the reaction mixture was concentrated under vacuum and product 1 was purified over silica employing a methanol (MeOH) gradient with DCM. The purified mass of product 1 was 16.5 g, a yield of 80%.

Fmoc-deprotection of Product 1: A mass of 16.5 g of product 1 (0.026453 moles; 1.0 equivalents) was dissolved in 80 mL of DCM. After which 20 mL of piperidine (0.23488 moles; 8.9 equivalents) was added to the reaction mixture and allowed to stir at room temperature under Ar(g). The reaction was monitored by TLC until completion. Product 2 was concentrated under vacuum and purification was attempted over silica. The impure mass of product 2 was 10.83 g.

Condensation of Product 2 with Lauric Acid: A mass of 10.83 g of product 2 (0.026973 moles; 1.0 equivalents) and 11.29 g of HATU (0.029692 moles; 1.1 equivalents) was dissolved in 120 mL of DCM. To this a mass of 5.95 g of lauric acid (0.029702 moles; 1.1 equivalents) was added to the reaction mixture. To promote the condensation reaction, 14.0 mL of DIEA (0.080377 moles; 3.0 equivalents) was added to the reaction mixture and allowed to stir for 24 hours at room temperature under Ar(g). The reaction was followed by thin-layer chromatography by monitoring the consumption of reactants and production of product 3. Upon completion, the reaction mixture was concentrated under vacuum and product 3 was purified over silica employing an ethyl acetate (EtOAc) gradient with heptane. The purified mass of product 3 was 7.0 g, a yield of 44%.

Boc-group Deprotection of Product 3: A mass of 7.0 g of product 3 (0.011990 moles; 1.0 equivalents) was dissolved in dioxane. To this, 50 mL of 12.1 M concentration hydrochloridic acid (HCl; 0.60500 moles; 50.1 equivalents) was added to the reaction mixture. The reaction was stirred for 2 hours at room temperature under Ar(g). Upon completion of the reaction a significant amount of product3 remained with respect to product 4. Therefore, the reaction mixture was concentrated, and the reaction was repeated for 30 minutes to ensure complete conversion of product3 to product4. After near complete conversion was observed, the reaction was concentrated under vacuum and purified over silica employing a MeOH gradient with DCM. The final purified mass of product 4, the desired product, was 2.77 g, a yield of 60%. Complete $^1$H-NMR, LC/MS and flow injection positive mode ESI-MS was performed to confirm the identity of the product.

In general, the reaction scheme that can be employed is shown below. Here, the Fmoc-protect amino acid can be couple to any primary (or secondary amine) with any one of the various coupling agents to amidate the carboxylic acid. Following deprotection of the Fmoc-group with piperidine, the amine on the amino acid can be acetylated with any carboxylic acid employing any one of the plethora of coupling agents. Finally, deprotection of any side chain protection groups can be performed by utilizing a strong acid.

Generalized Amino Acid Surfactant Reaction Scheme

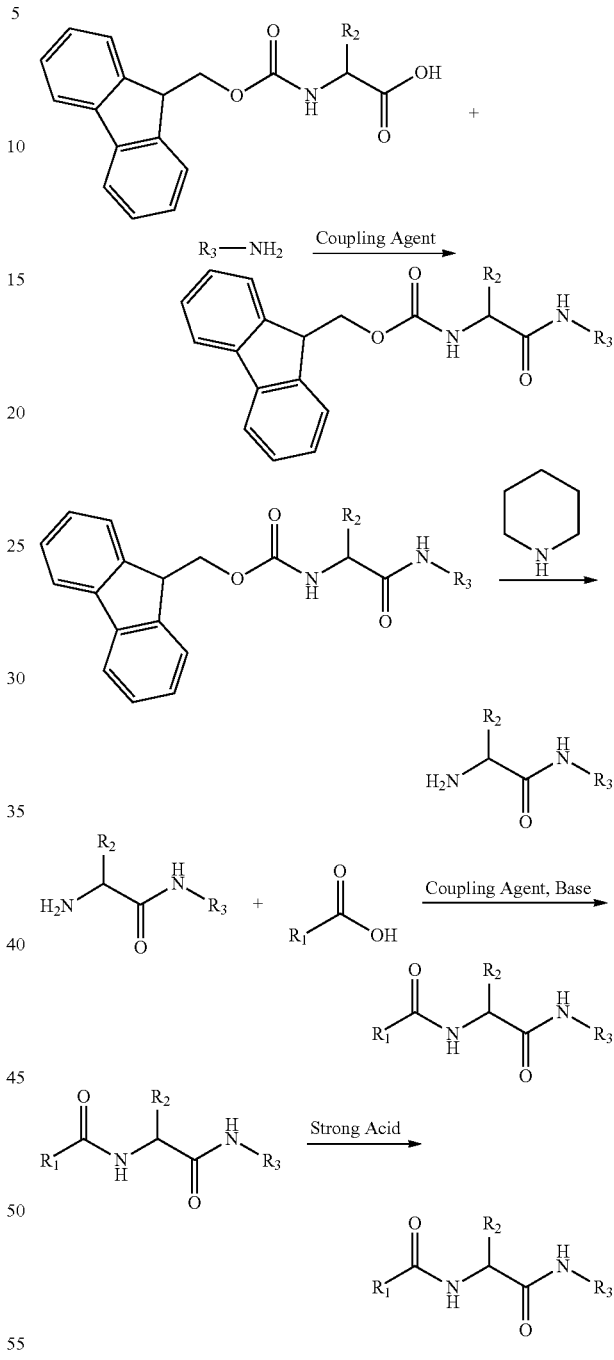

Figure 2:
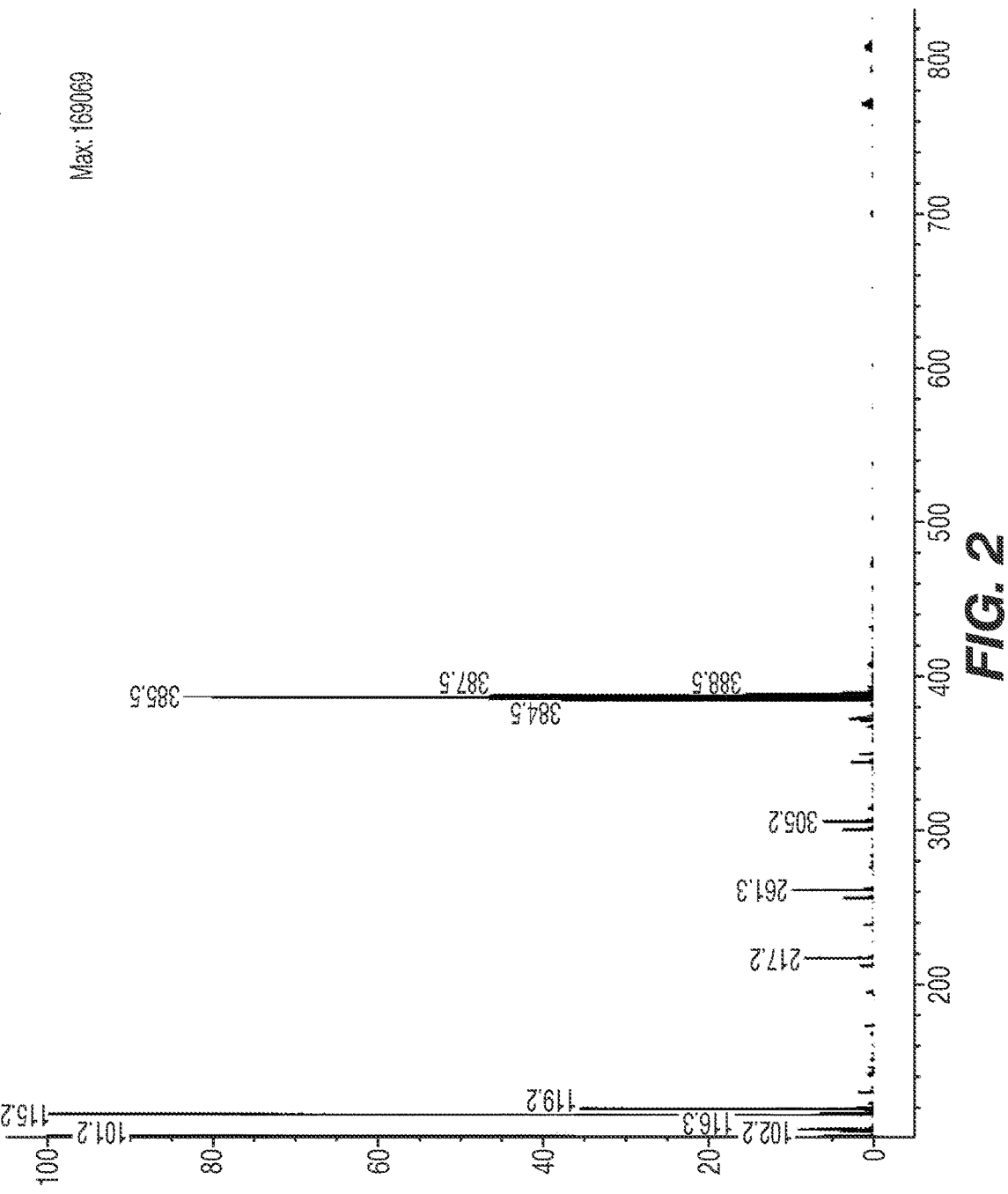
FIG. 2 is a drawing of the chemical structure and mass spectrometry graph of [amino({[4-dodecanamido-4-(ethylcarbamoyl)butyl]amino})methylidene]azanium.
Figure 3:
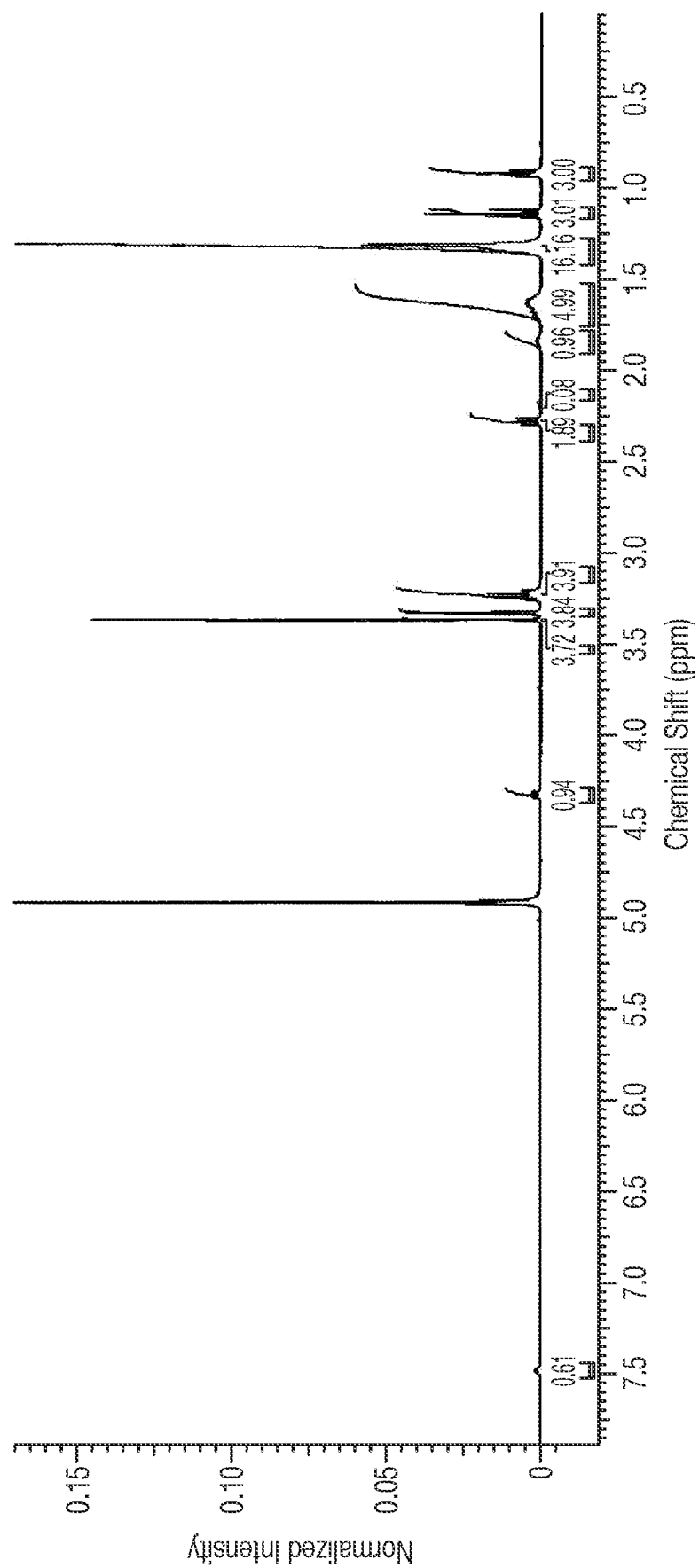
FIG. 3: is a $^1$H-NMR graph of [amino({[4-dodecanamido-4-(ethylcarbamoyl)butyl]amino})methylidene]azanium.

As further illustrated in FIGS. 1-3, the resulting purified product was measured using HPLC monitoring absorbance at 220 nm wavelength, mass spectrometry, and proton NMR in $D_2O$ using a 400 MHz Bruker instrument with 16 scans and identified as [amino({[4-dodecanamido-4-(ethylcarbamoyl)butyl]amino})methylidene]azanium. Shown in FIG. 1 is the LC/MS of purified compound 9. (A) HPLC chromatogram monitoring absorbance at 220 nm wavelength. (B) The corresponding positive mode electrospary ionization mass spectrometry of the primary peak highlighted in the red dotted line box. The calculated m/z for the [M+H]$^+$ of compound 9 is calculated to be 384.58727. Shown in FIG. 2 is: (A) The chemical structure and corresponding [M+H]⁺ m/z for compound 9. (B) Positive mode ESI-MS of compound 9 final product. Shown in FIG. 3 is: $^1$H-NMR of compound 9 in $D_2O$ on 400 MHz Bruker instrument with 16 scans.

Example 2: Dose Response of Compound 9 Prevention of Bacterial Attachment

Compositions A-F comprising different concentrations of compound 9 in water are shown in Table 1.

TABLE 1

Formulation compositions used in Example 2

| Composition | A | B | C | D | E | F |
|---|---|---|---|---|---|---|
| Compound 9 (w/w %) | 0.4 | 0.3 | 0.15 | 0.1 | 0.05 | 0.01 |
| Purified Water (w/w %) | 99.6 | 99.7 | 99.85 | 99.9 | 99.95 | 99.99 |

Initial studies evaluated the concentration effect of compound 9 in a simple water solution (Table 1 compositions) on prevention of bacterial attachment to pellicle coated HA pegs. Compound 9 in water demonstrated a dose dependent response and the most effective concentration was identified to be 0.3 wt % (Table 2). However, 0.15 wt % compound 9 also demonstrated efficacy at preventing bacterial attachment and was evaluated at that concentration further to match the concentration of LAE in the current commercial product, Listerine Advanced Defense Gum Health (positive control).

TABLE 2

Prevention assay efficacy results for compositions in Table 1

| Composition | A | B | C | D | E | F | Positive Control | Negative Control |
|---|---|---|---|---|---|---|---|---|
| Average Log RLU | 3.44 | 3.25 | 4.86 | 5.59 | 5.52 | 5.95 | 4.09 | 6.20 |
| Std Error | — | — | — | — | — | — | 0.14 | 0.15 |

Example 3: Compound 9 Prevents Bacterial Attachment Equivalent to LAE

The optimal concentration of compound 9 (0.15 wt %) was compared to the same concentration of LAE for prevention of bacterial attachment when formulated into a simple water or alcohol solution (Table 3).

TABLE 3

Formulation compositions used in Example 3

| Compositions | G | H | I | J |
|---|---|---|---|---|
| Compound 9 (w/w %) | 0.00 | 0.15 | 0.00 | 0.15 |
| LAE (w/w %) | 0.15 | 0.00 | 0.15 | 0.00 |
| Alcohol, 190 proof (w/w %) | 18.2 | 18.2 | 0 | 0 |
| Purified Water (w/w %) | 81.65 | 81.65 | 99.85 | 99.85 |

Table 4 suggests that compound 9 (0.15 wt %) is equally as efficacious as LAE (0.15 wt %) at preventing bacterial attachment in both a 21.6% alcohol and water-based solution. LAE concentration in Listerine Advanced Defense Gum Treatment (LAGDT) is 0.15 wt % which was the positive control with water as the negative control.

TABLE 4

Comparison between LAE and compound 9 in the prevention of bacterial attachment

| Compositions | G | H | I | J | 21.6% Alcohol Control | (Positive Control) | (Negative Control) |
|---|---|---|---|---|---|---|---|
| Average Log RLU | 4.35 | 4.75 | 4.85 | 4.59 | 5.96 | 4.09 | 6.20 |
| Std Error | — | — | 0.26 | 0.47 | — | 0.14 | 0.15 |

Example 4: Compound 9 Prevents Bacterial Attachment in Full Formula

Following confirmation that LAE prevents bacterial attachment to the same degree as LAE by the same mechanism of action, full formulas with compound 9 were optimized. Compound 9 compositions K-R include 0.15 wt % compound 9 in alcohol free base (Table 5).

TABLE 5

Formulation compositions used in example 3.

| Composition | K | L | M | N | O | P | Q | R |
|---|---|---|---|---|---|---|---|---|
| Compound 9 (w/w %) | 0.15 | 0.15 | 0.15 | 0.15 | 0.15 | 0.15 | 0.15 | 0.15 |
| L-Menthol, USP (w/w %) | 0.0039 | 0.0000 | 0.0039 | 0.0000 | 0.0039 | 0.0000 | 0.0039 | 0.0000 |
| Thymol NF (w/w %) | 0.0062 | 0.0000 | 0.0062 | 0.0000 | 0.0062 | 0.0000 | 0.0062 | 0.0000 |
| Methyl Salicylate NF (w/w %) | 0.0064 | 0.0000 | 0.0064 | 0.0000 | 0.0064 | 0.0000 | 0.0064 | 0.0000 |
| Eucalyptol USP (w/w %) | 0.0090 | 0.0000 | 0.0090 | 0.0000 | 0.0090 | 0.0000 | 0.0090 | 0.0000 |
| Pluracare F-127 NF Prill (w/w %), Polyethylene oxide co-propylene oxide | 0.20 | 0.20 | 0.20 | 0.20 | 0.00 | 0.00 | 0.00 | 0.00 |
| Mackam (w/w %) (31% LAURAMIDOPROPYL BETAINE, 62.7% water, 5.4% sodium chloride) | 0.00 | 0.00 | 0.65 | 0.65 | 0.65 | 0.65 | 0.00 | 0.00 |
| Benzoic Acid (w/w %) | 0.05 | 0.05 | 0.05 | 0.05 | 0.05 | 0.05 | 0.05 | 0.05 |
| Sodium Benzoate, NF/FCC Dense Form (w/w %) | 0.11 | 0.11 | 0.11 | 0.11 | 0.11 | 0.11 | 0.11 | 0.11 |

TABLE 5-continued

Formulation compositions used in example 3.

| Composition | K | L | M | N | O | P | Q | R |
|---|---|---|---|---|---|---|---|---|
| Sucralose(w/w %), 1,6-Dichloro-1,6-dideoxy-β-D-fructofuranosyl-4-chloro-4-deoxy-α-D-galactopyranoside | 0.01 | 0.01 | 0.01 | 0.01 | 0.01 | 0.01 | 0.01 | 0.01 |
| Sorbitol 70%, USP (w/w %), (2S,3R,4R,5R)-Hexane-1,2,3,4,5,6-hexol | 10.00 | 10.00 | 10.00 | 10.00 | 10.00 | 10.00 | 10.00 | 10.00 |
| Propylene Glycol, USP (w/w %) | 7.00 | 7.00 | 7.00 | 7.00 | 7.00 | 7.00 | 7.00 | 7.00 |
| Intensate Sweet Mint II, SF MOD (w/w %) | 0.02 | 0.00 | 0.02 | 0.00 | 0.02 | 0.00 | 0.02 | 0.00 |
| Purified Water (w/w %) | 82.43 | 82.48 | 81.79 | 81.83 | 81.99 | 82.03 | 82.63 | 82.68 |
| Final pH | 4.20 | 4.20 | 4.20 | 4.20 | 4.20 | 4.20 | 4.20 | 4.20 |

The results in Table 6 suggest that the presence of essential oils (EOs) has no effect on compound 9 (0.15 wt %) prevention of bacterial attachment. However, surfactant has a major effect with 0.645 wt % Mackam and no surfactant enabling the best prevention of attachment. LAE concentration in Listerine Advanced Defense Gum Treatment (LAGDT) is 0.15 wt % which is the positive control with water as the negative control.

TABLE 6

Prevention efficacy of formulations in Table 5.

| Compositions | K | L | M | N | O | P | Q | R | Positive Control | Negative Control |
|---|---|---|---|---|---|---|---|---|---|---|
| Average Log RLU | 4.70 | 4.88 | 4.33 | 4.39 | 4.08 | 4.17 | 3.82 | 3.65 | 4.09 | 6.20 |
| Std Error | — | — | — | — | — | — | — | — | 0.14 | 0.15 |

Example 5: Compound 9 Maintains Stability in an Alcohol-Free Formulation while LAE does not Select formulations (Table 7) were further evaluated for stability following incubation at 50° C. for 4 weeks by HPLC.

TABLE 7

Formulation compositions for Example 5.

| Composition | S | L | I | J |
|---|---|---|---|---|
| L-Menthol, USP (w/w %) | 0.0039 | 0.0039 | 0 | 0 |
| Thymol NF (w/w %) | 0.0062 | 0.0062 | 0 | 0 |
| Methyl Salicylate NF (w/w %) | 0.0064 | 0.0064 | 0 | 0 |
| Eucalyptol USP (w/w %) | 0.0090 | 0.0090 | 0 | 0 |
| Pluracare F-127 NF Prill (w/w %), Polyethylene oxide co-propylene oxide | 0.20 | 0.20 | 0 | 0 |
| Benzoic Acid (w/w %) | 0.05 | 0.05 | 0 | 0 |
| Sodium Benzoate, NF/FCC Dense Form (w/w %) | 0.11 | 0.11 | 0 | 0 |
| Sucralose(w/w %), 1,6-Dichloro-1,6-dideoxy-β-D-fructofuranosyl-4-chloro-4-deoxy-α-D-galactopyranoside | 0.01 | 0.01 | 0 | 0 |
| Sorbitol 70%, USP (w/w %), (2S,3R,4R,5R)-Hexane-1,2,3,4,5,6-hexol | 10.00 | 10.00 | 0 | 0 |
| Propylene Glycol, USP (w/w %) | 7.00 | 7.00 | 0 | 0 |
| Intensate Sweet Mint II, SF MOD (w/w %) | 0.017 | 0.017 | 0 | 0 |
| LAE (w/w %) | 0.15 | 0 | 0.15 | 0 |
| Compound 9 (w/w %) | 0 | 0.15 | 0 | 0.15 |
| Purified Water (w/w %) | 82.43 | 82.43 | 99.85 | 99.85 |
| Final pH | 4.37 | 4.37 | — | — |

Table 9 shows that compound 9 containing formulations are able maintain at least 90% compound 9 out to 8 weeks when stored at 50° C. as opposed to LAE which shows only 46 and 73% stability of the molecule after that length of storage (determined by HPLC).

TABLE 9

Compound 9 is stable in alcohol free formulation compositions.

| | % of Compound Remaining Following Storage at 50° C. | | | |
|---|---|---|---|---|
| | Week 0 | Week 2 | Week 4 | Week 8 |
| Composition S | 99 | 85 | 69 | 46 |
| Composition L | 104 | 95 | 93 | 92 |
| Composition I | 99 | 73 | 72 | 73 |
| Composition J | 100 | 90 | 98 | 106 |

Example 6: Compounds 1, 2, 3, 4, 6, 9, 11, 12, 16, 17, 18, 19, 20, 21, 22, 23, 24, 25, and 26 Prevent Bacterial Attachment A broader set of compounds (compounds 1-26) were evaluated for their ability to prevent bacterial attachment on a pellicle coated hydroxyapatite pegs. The results in Table 10 suggest that compounds 1, 2, 3, 4, 6, 9, 11, 12, 16, 17, 18, 19, 20, 21, 22, 23, 24, 25, and 26 have the ability to prevent bacterial attachment with compounds 1, 2, 3, 6, 9, 12, 17, 18, 19, 21, 22, and 26 preventing bacterial attachment the best. All tests were done in simple solution solvent base formulas (Table 11). Listerine Advanced Defense Gum Treatment (LAGDT) is the positive control with water as the negative control.

Example 7: Compounds 1 and 3-13 are Stable in Simple Solution Formulations (Table 13) and Compounds 1, 2, 3, 4, 6, 7, 9, 11 and 12 do not Result in More than a One Log Reduction in *S. mutans*

Compounds 1, 2, 3, 4, 6, 7, 9, 11 and 12 were evaluated in an in-vitro single species *S. mutans* biofilm model (Table 12 row 2). All compounds tested do not result in more than a one log reduction in *S. mutans*. Listerine Cool Mint was the positive control with water as the negative control. Compounds 1-13 were evaluated for structural stability via HPLC after storage at 50° C. for 4 and 8 weeks (Table 12 rows 3 and 4). All compounds tested maintained stability with only compound 2 showing a significant decrease in peak area. All tests were done in simple solution solvent base formulas (Table 13).

TABLE 10

Prevention efficacy of formulations in Table 11.

| Compositions | T | U | V | W | X | Y | Z | A1 | B1 | C1 |
|---|---|---|---|---|---|---|---|---|---|---|
| Average Log RLU | 3.88 | 3.96 | 4.00 | 5.61 | 6.29 | 4.41 | 6.47 | 6.68 | 4.98 | 6.55 |
| Compositions | D1 | E1 | F1 | G1 | H1 | I1 | J1 | K1 | L1 | M1 |
| Average Log RLU | 5.77 | 4.40 | 6.13 | 5.97 | 5.82 | 5.74 | 3.50 | 3.86 | 3.51 | 5.00 |

| Compositions | N1 | O1 | P1 | Q1 | R1 | S1 | Positive Control | Negative Control |
|---|---|---|---|---|---|---|---|---|
| Average Log RLU | 3.57 | 4.64 | 5.64 | 5.67 | 5.36 | 3.83 | 4.44 | 6.42 |

TABLE 11

Formulation compositions used in Example 6.

| Composition (w/w %) | T Compound 1 | U Compound 2 | V Compound 3 | W Compound 4 | X Compound 5 | Y Compound 6 | Z Compound 7 |
|---|---|---|---|---|---|---|---|
| Compound | 0.3 | 0.1 | 0.3 | 0.1 | 0.3 | 0.15 | 0.15 |
| Purified Water | 99.70 | 99.90 | 99.70 | 99.90 | 99.70 | 99.85 | 79.85 |
| Ethanol | 0 | 0 | 0 | 0 | 0 | 0 | 20 |
| Propylene Glycol | 0 | 0 | 0 | 0 | 0 | 0 | 0 |

| Composition (w/w %) | A1 Compound 8 | B1 Compound 9 | C1 Compound 10 | D1 Compound 11 | E1 Compound 12 | F1 Compound 13 | G1 Compound 14 |
|---|---|---|---|---|---|---|---|
| Compound | 0.3 | 0.15 | 0.15 | 0.3 | 0.15 | 0.15 | 0.15 |
| Purified Water | 79.70 | 79.85 | 79.85 | 99.70 | 99.85 | 49.85 | 49.85 |
| Ethanol | 20 | 20 | 0 | 0 | 0 | 0 | 0 |
| Propylene Glycol | 0 | 0 | 20 | 0 | 0 | 50 | 50 |

| Composition (w/w %) | H1 Compound 15 | I1 Compound 16 | J1 Compound 17 | K1 Compound 18 | L1 Compound 19 | M1 Compound 20 | N1 Compound 21 |
|---|---|---|---|---|---|---|---|
| Compound | 0.15 | 0.15 | 0.15 | 0.15 | 0.15 | 0.15 | 0.15 |
| Purified Water | 49.85 | 99.85 | 99.85 | 99.85 | 99.85 | 79.85 | 99.85 |
| Ethanol | 0 | 0 | 0 | 0 | 0 | 20 | 0 |
| Propylene Glycol | 50 | 0 | 0 | 0 | 0 | 0 | 0 |

| Composition (w/w %) | O1 Compound 22 | P1 Compound 23 | Q1 Compound 24 | R1 Compound 25 | S1 Compound 26 |
|---|---|---|---|---|---|
| Compound | 0.15 | 0.15 | 0.15 | 0.15 | 0.15 |
| Purified Water | 99.85 | 99.85 | 99.85 | 79.85 | 99.85 |
| Ethanol | 0 | 0 | 0 | 20 | 0 |
| Propylene Glycol | 0 | 0 | 0 | 0 | 0 |

TABLE 12

S. mutans biofilm efficacy (row 2), compound stability after 4 weeks of storage at 50° C.
(row 3), and compound stability after 8 weeks of storage at 50° C. (row 4) of formulations in Table 13.

| Compositions | T1 | U1 | V1 | W1 | X1 | Y1 | Z1 | A2 | B2 | C2 |
|---|---|---|---|---|---|---|---|---|---|---|
| S. Mutans Average Log RLU | 5.90 | 5.84 | 6.13 | 6.16 | NT | 6.20 | 6.51 | NT | 6.12 | NT |
| % Stable Derivative at 4 weeks storage at 50° C. | 98.80 | 76.30 | 103.08 | 97.35 | 105.21 | 104.56 | 94.20 | 98.74 | 102.35 | 97.65 |
| % Stable Derivative at 8 weeks storage at 50° C. | 91.39 | 63.46 | 106.34 | 96.06 | 96.54 | 106.43 | 93.84 | 100.18 | 104.39 | 93.95 |

| Compositions | D2 | E2 | F2 | G2 | H2 | I2 | Positive Control | Negative Control |
|---|---|---|---|---|---|---|---|---|
| S. Mutans Average Log RLU | 5.56 | 6.02 | NT | NT | NT | NT | 3.86 | 6.43 |
| % Stable Derivative at 4 weeks storage at 50° C. | 98.38 | 119.74 | 123.65 | NT | NT | NT | — | — |
| % Stable Derivative at 8 weeks storage at5 0° C. | 100.69 | 90.48 | 121.83 | NT | NT | NT | — | — |

NT = composition not tested.

TABLE 13

Formulation compositions used in Example 7.

| Composition (w/w %) | T1 Compound 1 | U1 Compound 2 | V1 Compound 3 | W1 Compound 4 | X1 Compound 5 | Y1 Compound 6 | Z1 Compound 7 |
|---|---|---|---|---|---|---|---|
| Compound | 0.30 | 0.10 | 0.30 | 0.10 | 0.30 | 0.15 | 0.15 |
| Purified Water | 99.70 | 99.90 | 99.70 | 99.90 | 99.70 | 99.85 | 79.85 |
| Ethanol | 0 | 0 | 0 | 0 | 0 | 0 | 20 |
| Propylene Glycol | 0 | 0 | 0 | 0 | 0 | 0 | 0 |

| Composition (w/w %) | A2 Compound 8 | B2 Compound 9 | C2 Compound 10 | D2 Compound 11 | E2 Compound 12 | F2 Compound 13 | G2 Compound 14 |
|---|---|---|---|---|---|---|---|
| Compound | 0.30 | 0.15 | 0.15 | 0.30 | 0.15 | 0.15 | 0.15 |
| Purified Water | 99.70 | 79.85 | 79.85 | 99.70 | 99.85 | 49.85 | 49.85 |
| Ethanol | 0 | 20 | 0 | 0 | 0 | 0 | 0 |
| Propylene Glycol | 0 | 0 | 20 | 0 | 0 | 50 | 50 |

| Composition (w/w %) | H2 Compound 15 | I2 Compound 16 |
|---|---|---|
| Compound | 0.15 | 0.15 |
| Purified Water | 49.85 | 99.85 |
| Ethanol | 0 | 0 |
| Propylene Glycol | 50 | 0 |

Example 8: Compounds 1, 2, 3, 6, 9, 11 and 12 Prevent Bacterial Attachment when Tested in Alcohol Free Full Formulations (Table 15)

Some of the lead candidates at preventing bacterial attachment were further optimized in alcohol-free full formulations with water as the only solvent (Table 15) for their ability to prevent bacterial attachment with and without essential oils (EOs) (Table 14: J2-Q2 without EOs and Q2-W2 with EOs). All formulations tested prevent bacterial attachment better when formulated with EOs. Listerine Advanced Defense Gum Treatment (LAGDT) is the positive control with water as the negative control.

TABLE 14

Prevention efficacy of formulations in Table 15.

| Compositions | J2 | K2 | L2 | M2 | N2 | O2 | P2 | Q2 | R2 | S2 |
|---|---|---|---|---|---|---|---|---|---|---|
| Average Log RLU | 3.98 | 4.02 | 4.52 | 4.51 | 4.81 | 4.70 | NT | 3.68 | 3.60 | 3.61 |

| Compositions | T2 | U2 | V2 | W2 | Positive Control | Negative Control |
|---|---|---|---|---|---|---|
| Average Log RLU | 3.58 | 3.63 | 3.74 | 3.50 | 4.21 | 5.86 |

TABLE 15

Formulation compositions used in Example 8.

| Composition (w/w %) | J2 Compound 1 | K2 Compound 2 | L2 Compound 3 | M2 Compound 6 | N2 Compound 9 | O2 Compound 11 | P2 Compound 12 |
|---|---|---|---|---|---|---|---|
| Compound | 0.15 | 0.15 | 0.15 | 0.15 | 0.15 | 0.15 | 0.15 |
| Pluracare F-68 NF Prill (w/w %), Polyethylene oxide co-propylene oxide | 2.50 | 2.50 | 2.50 | 2.50 | 2.50 | 2.50 | 2.50 |
| Propylene glycol, USP | 0.00 | 0.00 | 0.00 | 0.00 | 0.00 | 0.00 | 0.00 |
| Sucralose(w/w %), 1,6-Dichloro-1,6-dideoxy-β-D-fructofuranosyl-4-chloro-4-deoxy-α-D-galactopyranoside | 0.059 | 0.059 | 0.059 | 0.059 | 0.059 | 0.059 | 0.059 |
| Benzoic Acid | 0.086 | 0.086 | 0.086 | 0.086 | 0.086 | 0.086 | 0.000 |
| Sodium Benzoate, NF/FCC Dense Form | 0.077 | 0.077 | 0.077 | 0.077 | 0.077 | 0.077 | 0.000 |
| L-Menthol, USP | 0.000 | 0.000 | 0.000 | 0.000 | 0.000 | 0.000 | 0.000 |
| Thymol NF | 0.000 | 0.000 | 0.000 | 0.000 | 0.000 | 0.000 | 0.000 |
| Methyl Salicylate NF | 0.000 | 0.000 | 0.000 | 0.000 | 0.000 | 0.000 | 0.000 |
| Eucalyptol USP | 0.000 | 0.000 | 0.000 | 0.000 | 0.000 | 0.000 | 0.000 |
| Garbanzo 8 EC MOD, UT264932/00 | 0.000 | 0.000 | 0.000 | 0.000 | 0.000 | 0.000 | 0.000 |
| Purified water | 97.13 | 97.13 | 97.13 | 97.13 | 97.13 | 97.13 | 97.29 |

| Composition (w/w %) | Q2 Compound 1 | R2 Compound 2 | S2 Compound 3 | T2 Compound 6 | U2 Compound 9 | V2 Compound 11 | W2 Compound 12 |
|---|---|---|---|---|---|---|---|
| Compound | 0.15 | 0.15 | 0.15 | 0.15 | 0.15 | 0.15 | 0.15 |
| Pluracare F-68 NF Prill (w/w %), Polyethylene oxide co-propylene oxide | 2.50 | 2.50 | 2.50 | 2.50 | 2.50 | 2.50 | 2.50 |
| Propylene glycol, USP | 0.00 | 0.00 | 0.00 | 0.00 | 0.00 | 0.00 | 0.00 |
| Sucralose(w/w %), 1,6-Dichloro-1,6-dideoxy-β-D-fructofuranosyl-4-chloro-4-deoxy-α-D-galactopyranoside | 0.059 | 0.059 | 0.059 | 0.059 | 0.059 | 0.059 | 0.059 |
| Benzoic Acid | 0.086 | 0.086 | 0.086 | 0.086 | 0.086 | 0.086 | 0.000 |
| Sodium Benzoate, NF/FCC Dense Form | 0.077 | 0.077 | 0.077 | 0.077 | 0.077 | 0.077 | 0.000 |
| L-Menthol, USP | 0.020 | 0.020 | 0.020 | 0.020 | 0.020 | 0.020 | 0.020 |
| Thymol NF | 0.018 | 0.018 | 0.018 | 0.018 | 0.018 | 0.018 | 0.018 |
| Methyl Salicylate NF | 0.070 | 0.070 | 0.070 | 0.070 | 0.070 | 0.070 | 0.070 |
| Eucalyptol USP | 0.017 | 0.017 | 0.017 | 0.017 | 0.017 | 0.017 | 0.017 |
| Garbanzo 8 EC MOD, UT264932/00 | 0.088 | 0.088 | 0.088 | 0.088 | 0.088 | 0.088 | 0.088 |
| Purified water | 96.92 | 96.92 | 96.92 | 96.92 | 96.92 | 96.92 | 97.08 |

Example 9: Compounds 1, 2, 3, 6, 9, 11 and 12 Prevent Bacterial Attachment when Tested in Alcohol-Free Full Formulations (Table 17)

The lead candidates at preventing bacterial attachment were further optimized in alcohol-free full formulations with water and propylene glycol as the solvents (Table 17) for their ability to prevent bacterial attachment with and without essential oils (EOs) (Table 16: X2-D3 without EOs and E3-K3 with EOs). All formulations tested prevent bacterial attachment better when formulated with EOs. Listerine Advanced Defense Gum Treatment (LAGDT) is the positive control with water as the negative control.

TABLE 16

Prevention efficacy of formulations in Table 17.

| Compositions | X2 | Y2 | Z2 | A3 | B3 | C3 | D3 | E3 | F3 | G3 |
|---|---|---|---|---|---|---|---|---|---|---|
| Average Log RLU | 4.67 | 3.50 | 5.18 | 4.65 | 4.94 | 5.23 | 3.51 | 3.49 | 3.38 | 3.53 |

| Compositions | H3 | I3 | J3 | K3 | Positive Control | Negative Control |
|---|---|---|---|---|---|---|
| Average Log RLU | 3.67 | 3.60 | 3.99 | 3.30 | 4.31 | 6.12 |

TABLE 17

Formulation compositions used in Example 9.

| Composition (w/w %) | X2 Compound 1 | Y2 Compound 2 | Z2 Compound 3 | A3 Compound 6 | B3 Compound 9 | C3 Compound 11 | D3 Compound 12 |
|---|---|---|---|---|---|---|---|
| Compound | 0.15 | 0.15 | 0.15 | 0.15 | 0.15 | 0.15 | 0.15 |
| Pluracare F-68 NF Prill (P188), Polyethylene oxide co-propylene oxide | 1.00 | 1.00 | 1.00 | 1.00 | 1.00 | 1.00 | 1.00 |
| Propylene glycol, USP | 15.00 | 15.00 | 15.00 | 15.00 | 15.00 | 15.00 | 15.00 |
| Sucralose(w/w %), 1,6-Dichloro-1,6-dideoxy-β-D-fructofuranosyl-4-chloro-4-deoxy-α-D-galactopyranoside | 0.059 | 0.059 | 0.059 | 0.059 | 0.059 | 0.059 | 0.059 |
| Benzoic Acid | 0.086 | 0.086 | 0.086 | 0.086 | 0.086 | 0.086 | 0.011 |
| Sodium Benzoate, NF/FCC Dense Form | 0.077 | 0.077 | 0.077 | 0.077 | 0.077 | 0.077 | 0.010 |
| L-Menthol, USP | 0.000 | 0.000 | 0.000 | 0.000 | 0.000 | 0.000 | 0.000 |
| Thymol NF | 0.000 | 0.000 | 0.000 | 0.000 | 0.000 | 0.000 | 0.000 |
| Methyl Salicylate NF | 0.000 | 0.000 | 0.000 | 0.000 | 0.000 | 0.000 | 0.000 |
| Eucalyptol USP | 0.000 | 0.000 | 0.000 | 0.000 | 0.000 | 0.000 | 0.000 |
| Garbanzo 8 EC MOD, UT264932/00 | 0.000 | 0.000 | 0.000 | 0.000 | 0.000 | 0.000 | 0.000 |
| Purified water | 83.63 | 83.63 | 83.63 | 83.63 | 83.63 | 83.63 | 83.77 |

| Composition (w/w %) | E3 Compound 1 | F3 Compound 2 | G3 Compound 3 | H3 Compound 6 | I3 Compound 9 | J3 Compound 11 | K3 Compound 12 |
|---|---|---|---|---|---|---|---|
| Compound | 0.15 | 0.15 | 0.15 | 0.15 | 0.15 | 0.15 | 0.15 |
| Pluracare F-68 NF Prill (P188), Polyethylene oxide co-propylene oxide | 1.00 | 1.00 | 1.00 | 1.00 | 1.00 | 1.00 | 1.00 |
| Propylene glycol, USP | 15.00 | 15.00 | 15.00 | 15.00 | 15.00 | 15.00 | 15.00 |
| Sucralose(w/w %), 1,6-Dichloro-1,6-dideoxy-β-D-fructofuranosyl-4-chloro-4-deoxy-α-D-galactopyranoside | 0.059 | 0.059 | 0.059 | 0.059 | 0.059 | 0.059 | 0.059 |
| Benzoic Acid | 0.086 | 0.086 | 0.086 | 0.086 | 0.086 | 0.086 | 0.011 |
| Sodium Benzoate, NF/FCC Dense Form | 0.077 | 0.077 | 0.077 | 0.077 | 0.077 | 0.077 | 0.010 |
| L-Menthol, USP | 0.020 | 0.020 | 0.020 | 0.020 | 0.020 | 0.020 | 0.020 |
| Thymol NF | 0.018 | 0.018 | 0.018 | 0.018 | 0.018 | 0.018 | 0.018 |
| Methyl Salicylate NF | 0.070 | 0.070 | 0.070 | 0.070 | 0.070 | 0.070 | 0.070 |
| Eucalyptol USP | 0.017 | 0.017 | 0.017 | 0.017 | 0.017 | 0.017 | 0.017 |
| Garbanzo 8 EC MOD, UT264932/00 | 0.088 | 0.088 | 0.088 | 0.088 | 0.088 | 0.088 | 0.088 |
| Purified water | 83.57 | 83.57 | 83.57 | 83.57 | 83.57 | 83.57 | 83.71 |

Methods

Formulation Preparation

The formulations in Examples 2-9 were prepared using conventional mixing technology. Briefly, benzoic acid and sodium benzoate were dissolved in propylene glycol or water. Flavor and essential oils were dissolved in propylene glycol or in surfactant and water (in some compositions no EOs or flavor were added). Sucralose was dissolved in water. Surfactant was dissolved/mixed into water. The sodium benzoate and benzoic acid containing solution was added to the mixing vessel followed by the essential oil and flavor solutions and then the surfactant solution and sorbitol. This was followed by addition of the solid compound. Sonication or increase in temperature may or may not be used to expedite the dissolution of the compounds. The pH of the formulations was adjusted to about pH 4.2 with sodium hydroxide or hydrochloric acid and then water added to q.s. the composition.

Prevention Assay Method

The formulations in Examples 2-4, 6, 8 and 9 were prepared and test for prevention of bacterial attachment using the prevention assay. In this assay hydroxyapatite-coated polystyrene peg plate (96 pegs, N=8 per group) was exposed to saliva for one minute to form a pellicle at a temperature of 35 C. Then, for each formulation, eight pegs (N=8) were pre-treated for ten minutes with the formulation using an orbital shaker set to 500 RPM at room temperature. As a negative control, eight pegs (N=8) were pre-treated for ten minutes with sterile water. Next, a 16-hour salivary biofilm was grown on these polystyrene peg plates at a temperature of 35 C.

After all treatments were complete, the biofilm from each peg was neutralized and rinsed. The biofilm was harvested via sonication using a Q-Sonica Q700 Ultrasonic Liquid Processor with 431MP4-00 microplate horn Damper and 0.5:1 reverse gain booster (Q-Sonica, Newtown, Conn.). Using a Celsis Rapid Detection RapiScreen kit (Celsis International PLC, Chicago, Ill.), the bacteria were lysed with Celsis Luminex and then the adenosine triphosphate (ATP) from the lysed bacteria was measured using the bioluminescence marker Celcis Luminate and a Centro LB 960 Microplate Luminometer supplied by Berthold Technologies (Wildbad, Germany). Data were reported in log RLU (relative light units) where decreasing log RLUs indicated fewer viable bacteria remained on the biofilm substrate. The log RLUs for the prevention assay are shown on Tables 2, 4, 6, 10, 14, and 16.

S. mutans Single Species Kill Assay

The formulations listed in Example 7 were prepared and tested using an in-vitro single species S. mutans biofilm model. A 24-hour S. mutans biofilm is grown on a polystyrene peg plate (96 pegs, N=6 per test group). The pegs were subsequently treated for thirty seconds with each of formulations H and I, as well as positive and negative controls. The treatment is applied as a single thirty (30) second treatment. The positive control is a commercially available essential oil mouth rinse. The negative control is sterile water. After treatment the biofilm is neutralized and rinsed. The biofilm is harvested via sonication using a Misonix Ultrasonic Liquid Processor (Farmingdale, N.Y.). Using a Celsis Rapid Detection RapiScreen kit (Celsis International PLC, Chicago), the bacteria are lysed with Celsis Luminex and then the adenosine triphosphate (ATP) from the lysed bacteria is measured using the bioluminescence marker LB960 Microplate Luminometer supplied by Berthold (Wildbad, Germany). Data are reported in log RLU (relative light units) where decreasing log RLUs indicates fewer viable bacteria remaining on the biofilm substrate.

HPLC Quantification of Compounds

Briefly, formulations containing either LAE or any of the 26 compounds and standards are diluted into a solution of 50% acetonitrile and 50% water. They are evaluated on an Agilent HPLC using a Zorbax ion exchange column. In the method, 10 uL of the sample is withdrawn and ran through the HPLC with a 40% potassium phosphate (molarity at pH 3.0) 60% acetonitrile mobile phase. Sample retention time varies between 4 and 12 minutes, depending upon the molecule. The molecule peak is auto integrated using the Online Agilent HPLC software. Comparisons are made to the standard to identify the % of compound remaining following storage.

What is claimed is:

1. A method of inhibiting plaque in an oral cavity comprising contacting a surface of the oral cavity with a compound selected from the group consisting of:

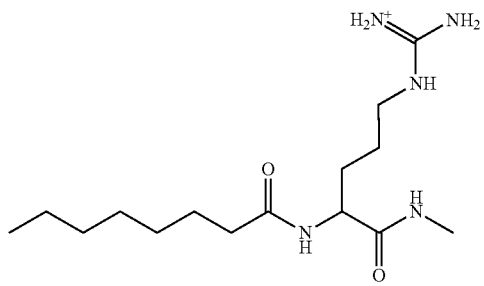

[amino({[4-(methylcarbamoyl)-4-octanamidobutyl] amino})methylidene]azanium,

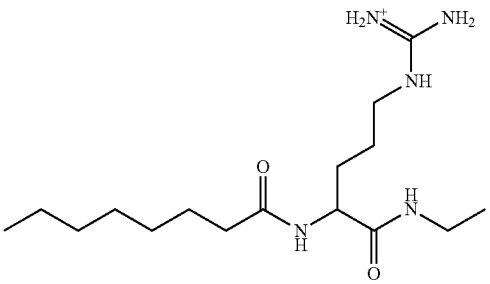 [SMILES: CCCCCCCC(=O)NC(CCCNC(N)=[NH2+])C(=O)NCC]

[amino({[4-(ethylcarbamoyl)-4-octanamidobutyl] amino})methylidene]azanium,

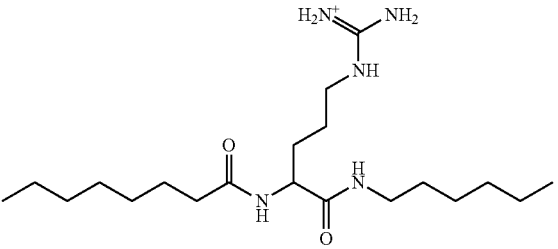 [SMILES: CCCCCCCC(=O)NC(CCCNC(N)=[NH2+])C(=O)NCCCCCC]

[amino({[4-(hexylcarbamoyl)-4-octanamidobutyl] amino})methylidene]azanium,

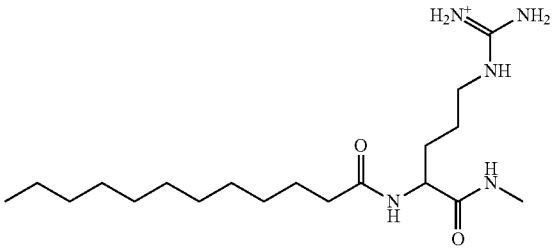 [SMILES: CCCCCCCCCCCC(=O)NC(CCCNC(N)=[NH2+])C(=O)NC]

[amino({[4-dodecanamido-4-(methylcarbamoyl)butyl] amino})methylidene]azanium,

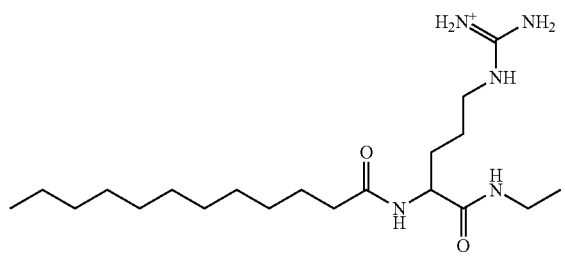 [SMILES: CCCCCCCCCCCC(=O)NC(CCCNC(N)=[NH2+])C(=O)NCC]

[amino({[4-dodecanamido-4-(ethylcarbamoyl)butyl]amino})methylidene]azanium,

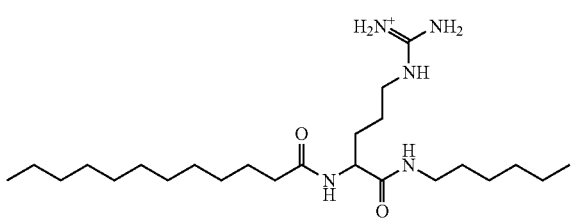 [SMILES: CCCCCCCCCCCC(=O)NC(CCCNC(N)=[NH2+])C(=O)NCCCCCC]

[amino({[4-dodecanamido-4-(hexylcarbamoyl)butyl]amino})methylidene]azanium,

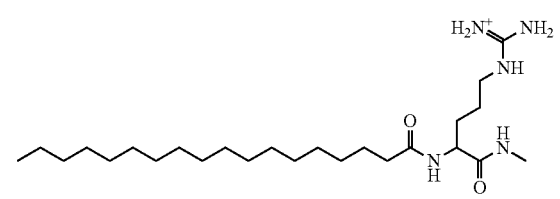 [SMILES: CCCCCCCCCCCCCCCCCC(=O)NC(CCCNC(N)=[NH2+])C(=O)NC]

[amino({[4-(methylcarbamoyl)-4-octadecanamidobutyl]amino})methylidene]azanium,

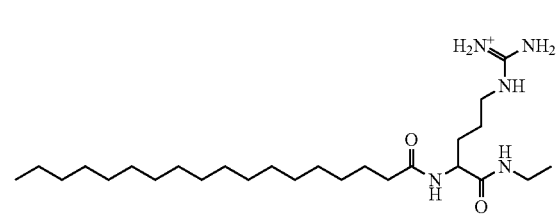 [SMILES: CCCCCCCCCCCCCCCCCC(=O)NC(CCCNC(N)=[NH2+])C(=O)NCC]

[amino({[4-(ethylcarbamoyl)-4-octadecanamidobutyl]amino})methylidene]azanium,

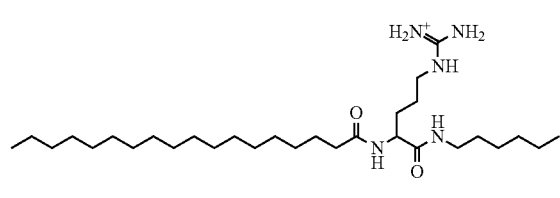 [SMILES: CCCCCCCCCCCCCCCCCC(=O)NC(CCCNC(N)=[NH2+])C(=O)NCCCCCC]

[amino({[4-(hexylcarbamoyl)-4-octadecanamidobutyl]amino})methylidene]azanium,

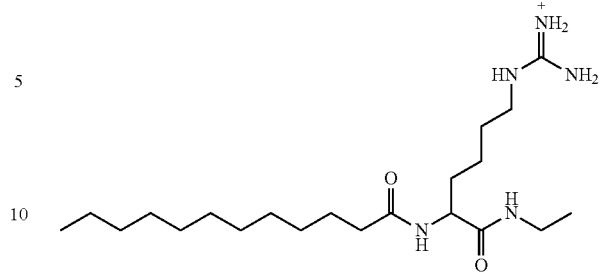

[amino({[5-dodecanamido-5-(ethylcarbamoyl)pentyl]amino})methylidene]azanium,

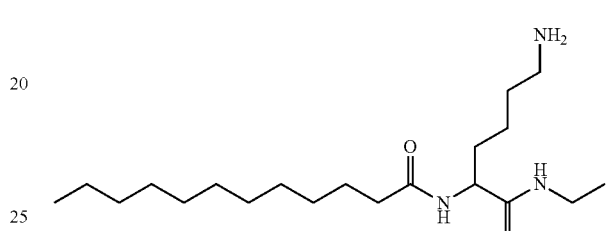

N-[5-amino-1-(ethylcarbamoyl)pentyl]dodecanamide,

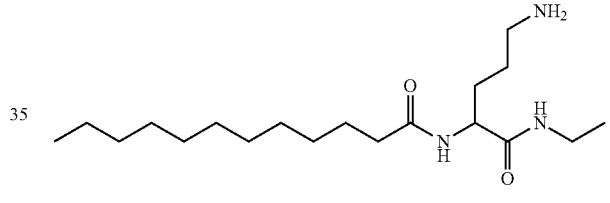

N-[4-amino-1-(ethylcarbamoyl)butyl]dodecanamide and

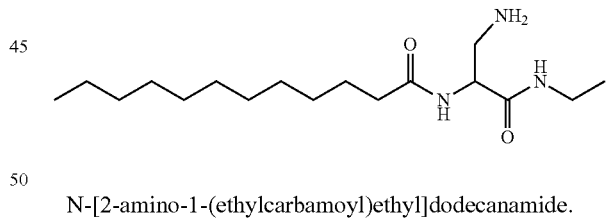

N-[2-amino-1-(ethylcarbamoyl)ethyl]dodecanamide.

2. The method of claim 1 wherein the compound is

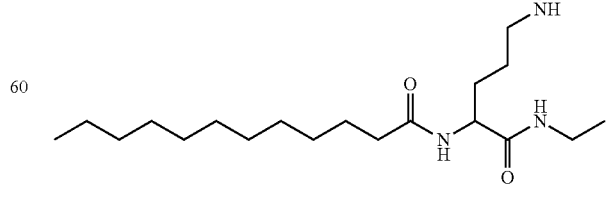

[amino({[4-dodecanamido-4-(ethylcarbamoyl)butyl]amino})methylidene]azanium.

3. A method of inhibiting plaque in an oral cavity comprising contacting a surface of the oral cavity with a compound selected from the group consisting of:

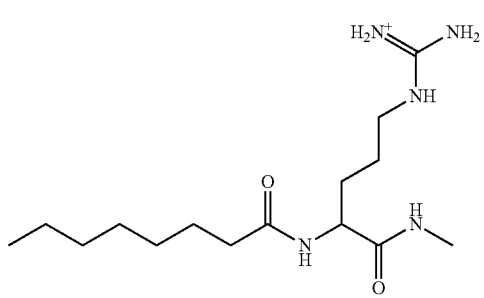 [SMILES: CCCCCCCC(=O)NC(CCCNC(N)=[NH2+])C(=O)NC]

[amino({[4-(methylcarbamoyl)-4-octanamidobutyl]amino})methylidene]azanium,

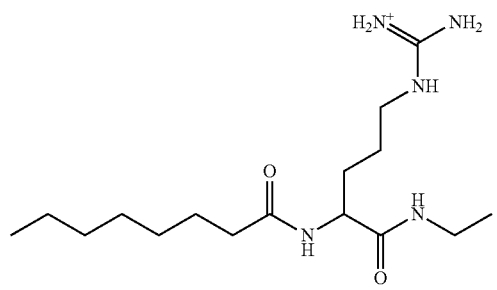 [SMILES: CCCCCCCC(=O)NC(CCCNC(N)=[NH2+])C(=O)NCC]

[amino({[4-(ethylcarbamoyl)-4-octanamidobutyl]amino})methylidene]azanium,

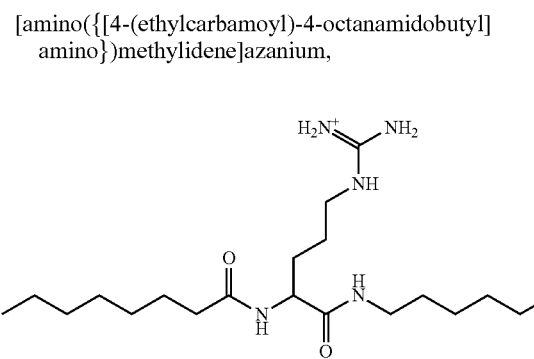

[amino({[4-(hexylcarbamoyl)-4-octanamidobutyl]amino})methylidene]azanium,

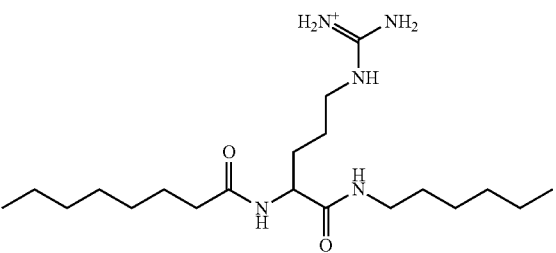 [SMILES: CCCCCCCC(=O)NC(CCCNC(N)=[NH2+])C(=O)NCCCCCC]

[amino({[4-dodecanamido-4-(methylcarbamoyl)butyl]amino})methylidene]azanium,

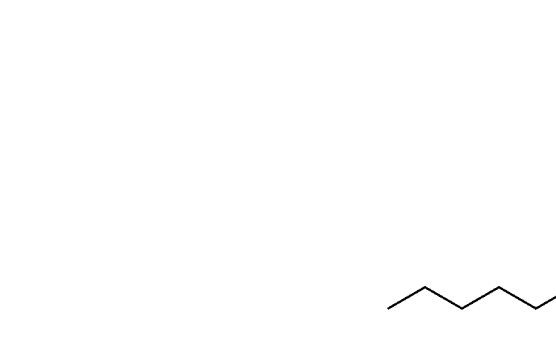

[amino({[4-dodecanamido-4-(ethylcarbamoyl)butyl]amino})methylidene]azanium,

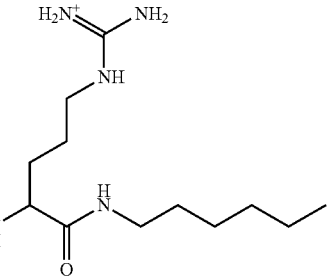

[amino({[4-dodecanamido-4-(hexylcarbamoyl)butyl]amino})methylidene]azanium,

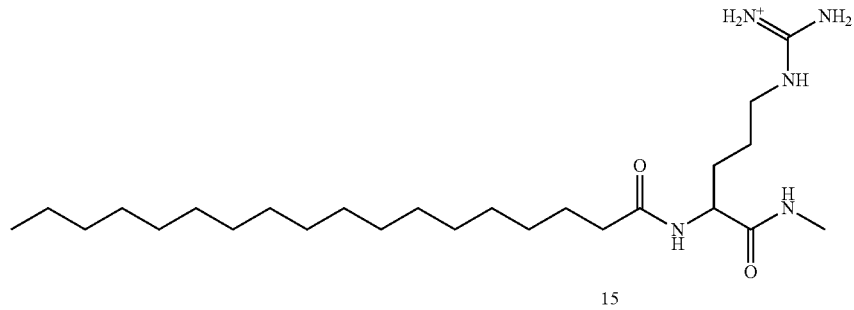

[amino({[4-(methylcarbamoyl)-4-octadecanamidobutyl]amino})methylidene]azanium,

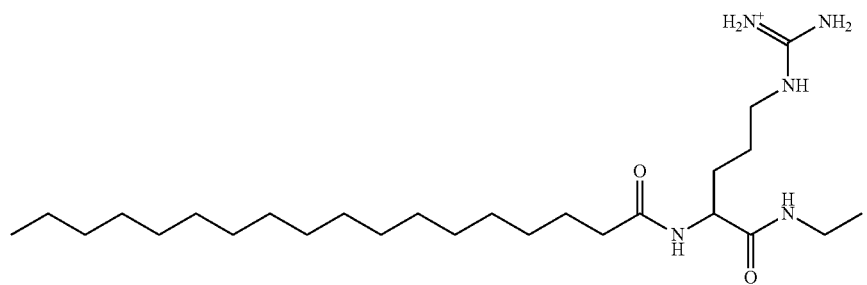 [SMILES: CCCCCCCCCCCCCCCCCC(=O)NC(CCCNC(N)=[NH2+])C(=O)NCC]

[amino({[4-(ethylcarbamoyl)-4-octadecanamidobutyl]amino})methylidene]azanium,

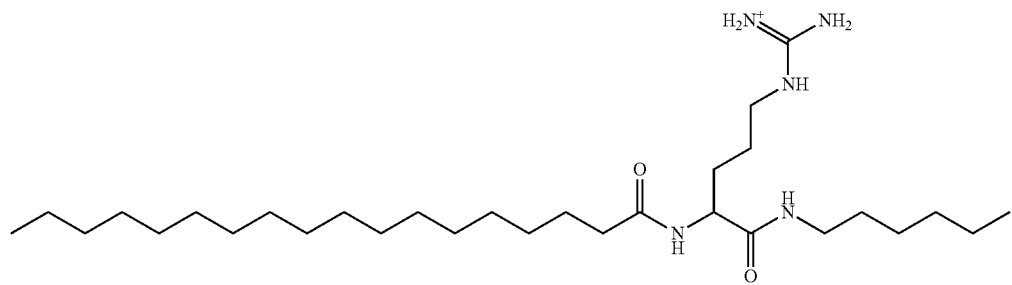 [SMILES: CCCCCCCCCCCCCCCCCC(=O)NC(CCCNC(N)=[NH2+])C(=O)NCCCCCC]

[amino({[4-(hexylcarbamoyl)-4-octadecanamidobutyl]amino})methylidene]azanium,

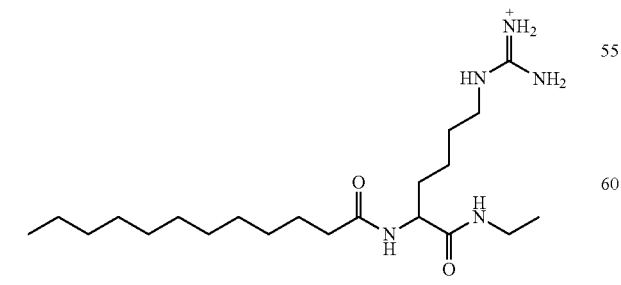

[amino({[5-dodecanamido-5-(ethylcarbamoyl)pentyl]amino})methylidene]azanium, and

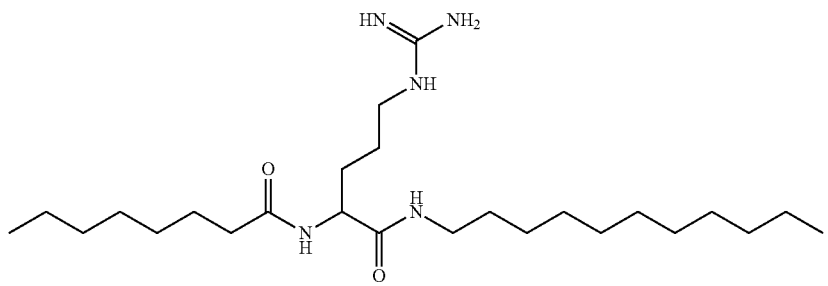 [SMILES: CCCCCCCCCCCNC(=O)C(CCCNC(=N)N)NC(=O)CCCCCCC]

N-(5-guanidino-1-oxo-1-(undecylamino)pentan-2-yl)octanamide.

4. A method of inhibiting plaque in an oral cavity comprising contacting a surface of the oral cavity with a compound selected from the group consisting of:

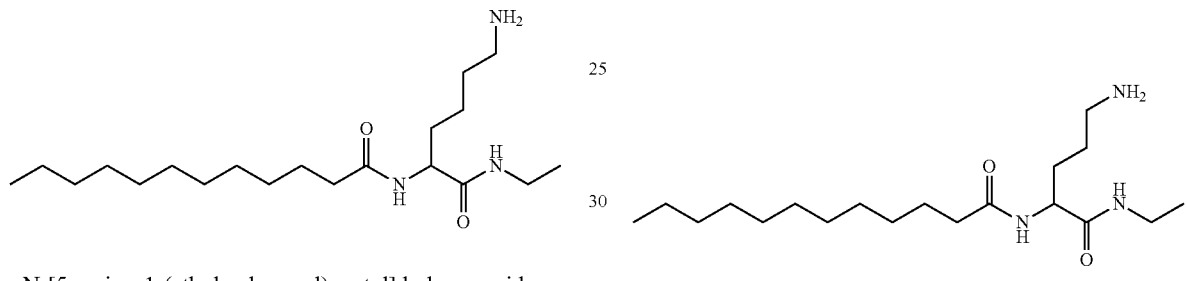

N-[5-amino-1-(ethylcarbamoyl)pentyl]dodecanamide,

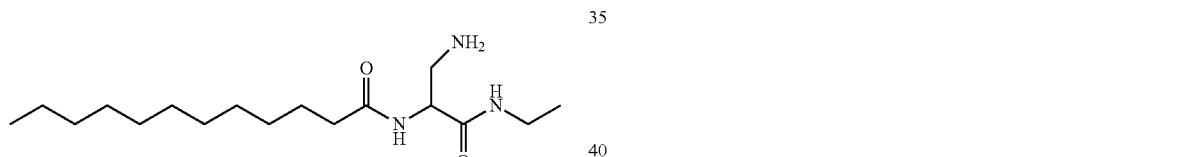

N-[2-amino-1-(ethylcarbamoyl)ethyl]dodecanamide,

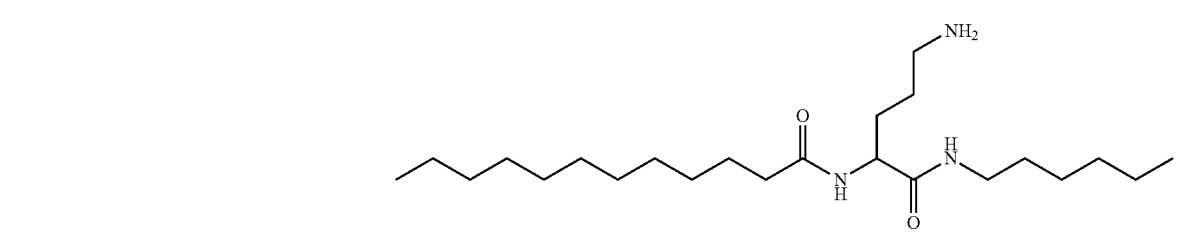 [SMILES: CCCCCCCCCCCC(=O)NC(CCCN)C(=O)NCCCCCC]

N-[4-amino-1-(ethylcarbamoyl)butyl]dodecanamide,

N-(5-amino-1-(hexylamino)-1-oxopentan-2-yl)dodecanamide,

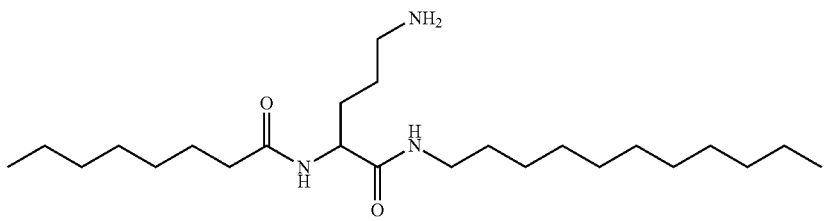 [SMILES: CCCCCCCCCCCNC(=O)C(CCCN)NC(=O)CCCCCCC]

N-(5-amino-1-oxo-1-(undecylamino)pentan-2-yl)octanamide
and
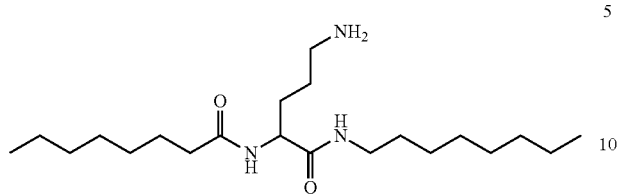
N-(5-amino-1-(octylamino)-1-oxopentan-2-yl)octanamide.
* * * * *